(12) United States Patent
Matsumoto et al.

(10) Patent No.: US 8,772,099 B2
(45) Date of Patent: Jul. 8, 2014

(54) METHOD OF USE OF A FIELD-EFFECT TRANSISTOR, SINGLE-ELECTRON TRANSISTOR AND SENSOR

(75) Inventors: Kazuhiko Matsumoto, Ibaraki (JP); Atsuhiko Kojima, Ibaraki (JP); Satoru Nagao, Chiba (JP); Masanori Katou, Kanagawa (JP); Yutaka Yamada, Ibaraki (JP); Kazuhiro Nagaike, Kanagawa (JP); Yasuo Ifuku, Kanagawa (JP); Hiroshi Mitani, Kanagawa (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 13/556,314

(22) Filed: Jul. 24, 2012

(65) Prior Publication Data

US 2012/0286763 A1 Nov. 15, 2012

Related U.S. Application Data

(63) Continuation of application No. 10/570,279, filed as application No. PCT/JP2004/012402 on Aug. 27, 2004, now Pat. No. 8,502,277.

(30) Foreign Application Priority Data

Aug. 29, 2003 (JP) .................................. 2003-307798

(51) Int. Cl.
*H01L 21/336* (2006.01)

(52) U.S. Cl.
USPC ............ 438/197; 438/1; 438/284; 257/E21.4; 257/E21.421

(58) Field of Classification Search
USPC ................... 257/253, E21.4, 421; 438/1, 197
See application file for complete search history.

(56) References Cited

U.S. PATENT DOCUMENTS

| 4,180,771 A | 12/1979 | Guckel |
| 5,492,840 A | 2/1996 | Malmqvist et al. |

(Continued)

FOREIGN PATENT DOCUMENTS

| EP | 1411554 | 4/2004 |
| JP | 54-161992 | 12/1979 |

(Continued)

OTHER PUBLICATIONS

Yasuo, JP10260156, 1998.*

(Continued)

*Primary Examiner* — Minchul Yang
(74) *Attorney, Agent, or Firm* — Katten Muchin Rosenman LLP

(57) ABSTRACT

A method of detecting a detection target using a sensor requires a sensor having a transistor selected from the group of field-effect transistors or single electron transistors. The transistor includes a substrate, a source electrode disposed on the substrate and a drain electrode disposed on the substrate, and a channel forming a current path between the source electrode and the drawing electrode; an interaction-sensing gate comprising a specific substance; and a voltage gate. The method includes (a) providing the detection target on the interaction-sensing gate; (b) setting the gate voltage in the voltage gate at a predetermined level; (c) selectively interacting the specific substance with the detection target; (d) when the detection target interacts with the specific substance, changing a gate voltage in the voltage gate to adjust a characteristic of the transistor; and (e) measuring a change in the characteristic of the transistor to determine a presence of the detection target.

4 Claims, 13 Drawing Sheets

(56) References Cited

U.S. PATENT DOCUMENTS

| | | | |
|---|---|---|---|
| 5,827,482 | A | 10/1998 | Shieh et al. |
| 6,472,705 | B1 | 10/2002 | Bethune et al. |
| 6,515,339 | B2 | 2/2003 | Shin et al. |
| 7,439,562 | B2 * | 10/2008 | Auvray et al. ............ 257/253 |
| 2002/0014667 | A1 | 2/2002 | Shin et al. |
| 2002/0024099 | A1 | 2/2002 | Watanabe et al. |
| 2003/0102510 | A1 | 6/2003 | Lim et al. |
| 2004/0036128 | A1 | 2/2004 | Zhang et al. |
| 2004/0238887 | A1 | 12/2004 | Nihey |
| 2005/0053524 | A1 * | 3/2005 | Keersmaecker et al. ....... 422/88 |

FOREIGN PATENT DOCUMENTS

| | | |
|---|---|---|
| JP | 57-161541 | 10/1982 |
| JP | 57-191539 | 11/1982 |
| JP | 58-19984 | 4/1983 |
| JP | 59-28648 | 2/1984 |
| JP | 60-39547 | 3/1985 |
| JP | 60-47952 | 3/1985 |
| JP | 61-89553 | 5/1986 |
| JP | 62-39756 | 2/1987 |
| JP | 62-132160 | 6/1987 |
| JP | 62-184345 | 8/1987 |
| JP | 62-232556 | 10/1987 |
| JP | 63-88438 | 4/1988 |
| JP | 1-201152 | 8/1989 |
| JP | 1-203959 | 8/1989 |
| JP | 2-280047 | 11/1990 |
| JP | 3-502135 | 5/1991 |
| JP | 5-72979 | 10/1993 |
| JP | 8-94577 | 4/1996 |
| JP | 2537354 | 7/1996 |
| JP | 8-278281 | 10/1996 |
| JP | 10-203810 | 8/1998 |
| JP | 2814639 | 8/1998 |
| JP | 10-260156 | 9/1998 |
| JP | 11-514748 | 12/1999 |
| JP | 2000-156423 | 6/2000 |
| JP | 2000-187017 | 7/2000 |
| JP | 2001-33423 | 2/2001 |
| JP | 2002-118248 | 4/2002 |
| JP | 2002-296229 | 10/2002 |
| JP | 2003-17508 | 1/2003 |
| JP | 2003-507889 | 2/2003 |
| JP | 2003-109974 | 4/2003 |
| WO | 90/01694 | 2/1990 |
| WO | 00/09443 | 2/2000 |
| WO | 01/13432 | 2/2001 |
| WO | 01/44796 | 6/2001 |
| WO | 02/48701 | 6/2002 |

OTHER PUBLICATIONS

English translation of Yasuo, JP10260156, 1998.*
"Bioluminescence and chemiluminescence", K. Imai, Hirokawa Shoten Ltd., pp. 170-185. Jan. 10, 1989.
"Biosensor", S. Suzuki, Kosansha Scientific, pp. 1-11. Mar. 10, 1984.
"Development and commercialization of sensor", I. Karube, Kagaku Kogyosha, pp. 1-18. Jan. 10, 1986.
International Search Report dated Nov. 9, 2004, from corresponding International Application No. PCT/JP2004/012402.
Kazuhiko Matsumoto. "Manfacturing and Device Application of Position Controlled Grown Carbon Nanotube" Oyo Buturi, Mar. 10, 2003, vol. 72, No. 3, pp. 331 to 332.
Kazuhiko Matsumoto. "New Development in the Area of Carbon Nanotube", Seisan Kenkyu, Jul. 2003, vol. 55, No. 4, pp. 358-365.
K. Matsumoto. National Institute of Advanced Industrial Science and Technology (AIST), Press Release published on Sep. 13, 2002 http://www.aist.go.jp/aist_i/press_release/pr2002/pr20020913/pr20020913.html.
Kazuhiko Matsumoto. "Position Controlled Grown Carbon Nanotube for SET & FED", Extended Abstracts (The 63rd Autumn Meeting, 2002); The Japan Society of Applied Physics No. 0, p. 13, Sep. 24, 2002.
Notification of Reasons for Rejection dated Apr. 20, 2010, from corresponding Japanese Application No. 2003-307798.
Supplementary Partial European Search Report dated Sep. 27, 2011, from corresponding European Application No. 04 77 2358.
Alexander Star, et al. "Electronic Detection of Specific Protein Binding Using Nanotube FET Devices" NANO Letters, ACS, vol. 3, No. 4, Jan. 1, 2003, pp. 459-463.
Kazuhiko Matsumoto, et al. "Single-Electron Transistor with Ultra-High Coulomb Energy of 5000 K Using Position Controlled Grown Carbon Nanotube as Channel" Japanese Journal of Applied Physics, vol. 42, No. 4B, Apr. 1, 2003, pp. 2415-2418.
United States Office Action dated Jul. 13, 2009, from corresponding U.S. Appl. No. 10/570,279.
United States Office Action dated Nov. 18, 2009, from corresponding U.S. Appl. No. 10/570,279.
United States Office Action dated Nov. 15, 2010, from corresponding U.S. Appl. No. 10/570,279.
United States Office Action dated Mar. 1, 2011, from corresponding U.S. Appl. No. 10/570,279.
United States Office Action dated Jun. 16, 2011, from corresponding U.S. Appl. No. 10/570,279.
United States Office Action dated Oct. 14, 2011, from corresponding U.S. Appl. No. 10/570,279.
Alexander Star, et al. "Electronic Detection of Specific Protein Binding Using Nanotube FET Devices" Nano Letters, 2003, vol. 3, No. 4 pp. 459-463.
Henk W. CH. Postma, et al. "Carbon Nanotube Single-Electron Transistors at Room Temperature" SCIENCE, vol. 293, Jul. 6, 2001, pp. 76-79.
English translation of JP 10260156 (previously made of record in IDS), Sep. 29, 1998.
United States Office Action dated Nov. 16, 2012, from corresponding U.S. Appl. No. 13/556,316.
United States Office Action dated Mar. 19, 2013, from corresponding U.S. Appl. No. 13/556,316.
United States Office Action dated Aug. 1, 2013, from corresponding U.S. Appl. No. 13/556,316.
Extended European Search Report, dated Feb. 4, 2014, from corresponding European Patent Application No. 13181482.4.
Martel R et al: "Single—and Multi-wall carbon nanotube field-effect transistors", Applied Physics Letters, American Institute of Physics, US, vol. 73, No. 17, Oct. 26, 1998, pp. 2447-2449, XP012021233, ISSN: 0003-6951, DOI: 10.1063/1. 122477.
Tans S J et al: "Room-Temperature Transistor Based on a Single Carbon Nanotube", Nature, Nature Publishing Group, United Kingdom, vol. 393, May 1 1998, pp. 49-52, XP002929421, ISSN: 0028-0836, DOI: 10.1038/29954.
Bradley K et al: "Influence of Mobile Ions on Nanotube Based Fet Devices", Nano Letters, American Chemical Society, US, vol. 3, No. 5, May 1, 2003, pp. 639-641, XP008043678, ISSN: 1530-6984, DOI: 10.1021/NL025941J.

* cited by examiner

FIG. 11
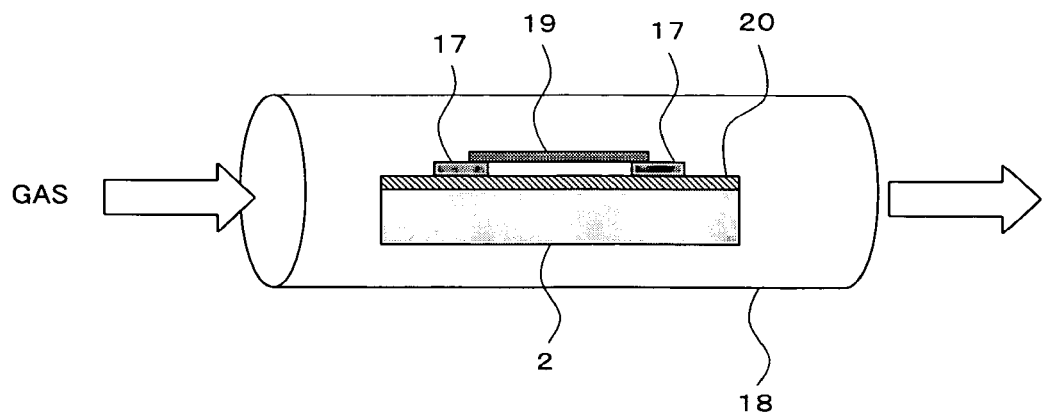
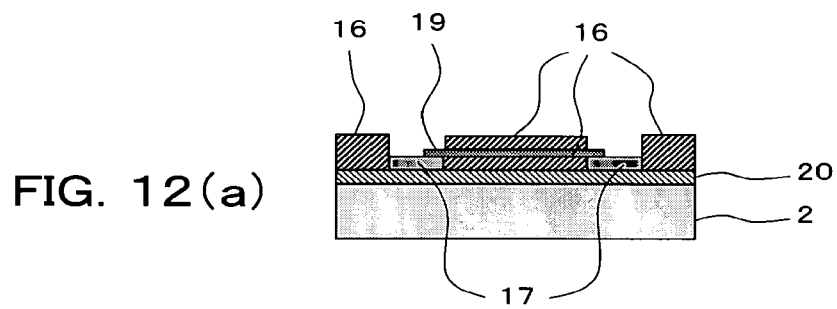
FIG. 12(a)
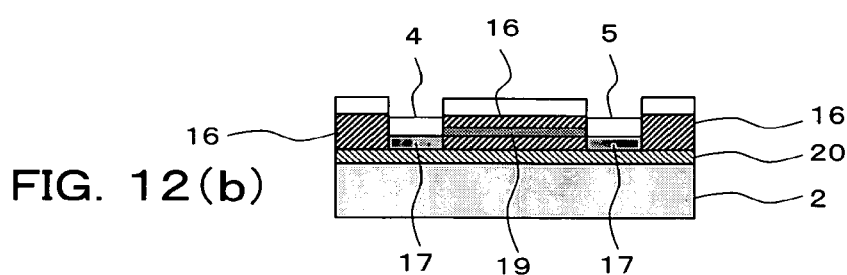
FIG. 12(b)
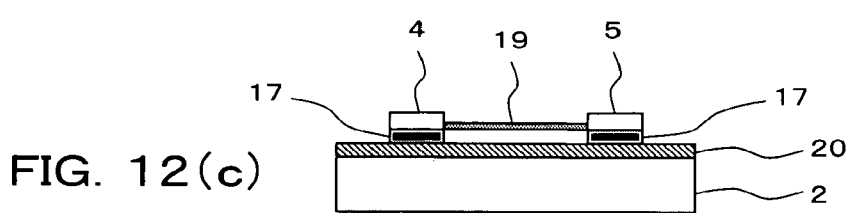
FIG. 12(c)

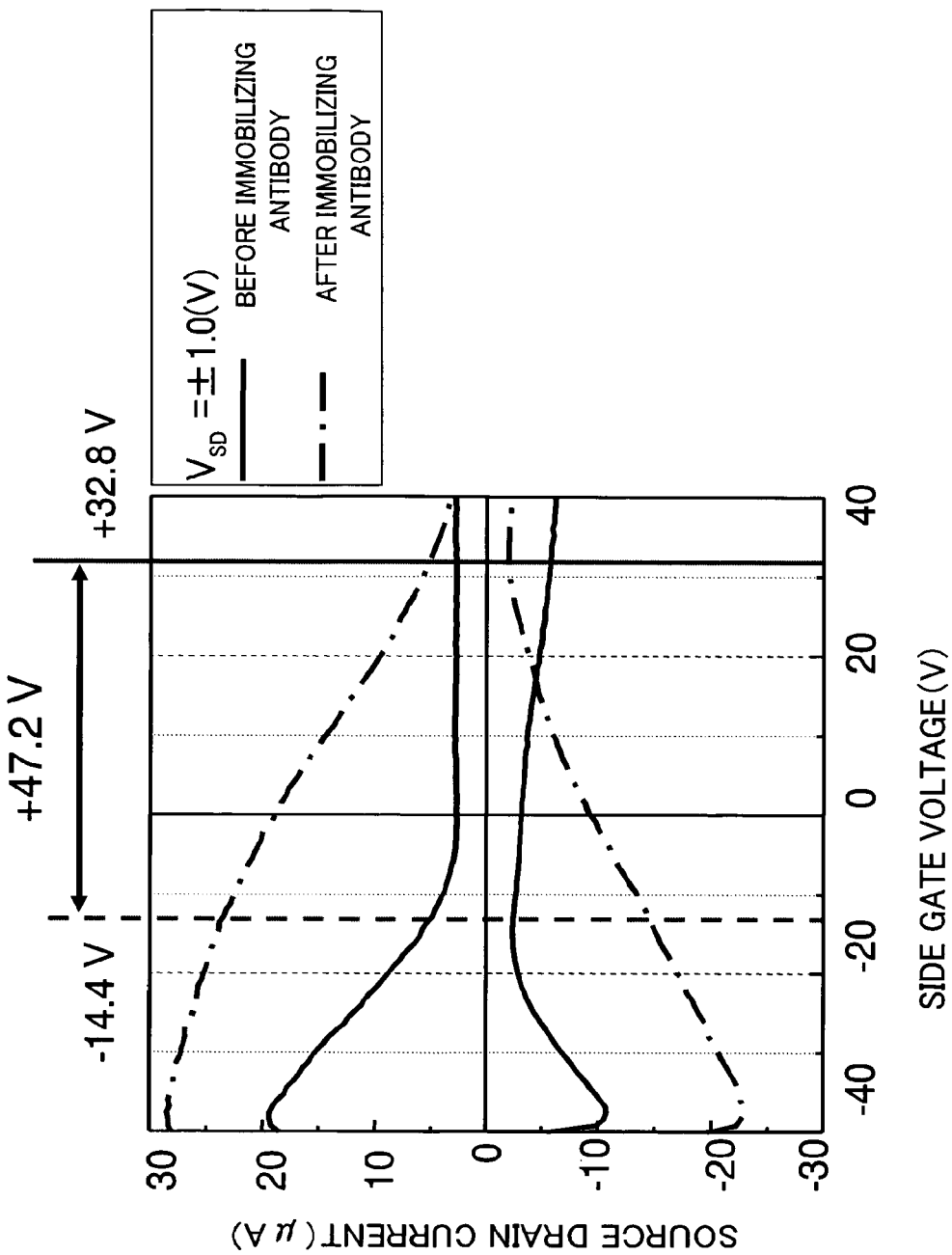

METHOD OF USE OF A FIELD-EFFECT TRANSISTOR, SINGLE-ELECTRON TRANSISTOR AND SENSOR

CROSS-REFERENCE TO RELATED APPLICATIONS

This application is continuation application of and claims priority from U.S. Ser. No. 10/570,279, filed on Nov. 2, 2006, which is pending and which is hereby incorporated in its entirety for all purposes.

U.S. Ser. No. 10/570,279 is a national stage entry of and claims priority from PCT/JP04/12402 filed Aug. 27, 2004.

BACKGROUND OF THE INVENTION

1. Field of the Invention

The present invention relates to a field-effect transistor, a single-electron transistor and a sensor using the same.

2. Discussion of the Related Art

A field-effect transistor (FET) and a single-electron transistor (SET) are elements that convert voltage signals input in a gate into current signals output from either a source electrode or a drain electrode. On placing a voltage between the source electrode and the drain electrode, charged particles existing in the channel move between the source electrode and the drain electrode along the direction of electric field and are output from either the source electrode or the drain electrode as a current signal.

At this point, the strength of the output current signal is proportional to the density of the charged particles. When a voltage is applied on the gate that is placed at upward, sideward or downward position of the channel with an insulator therebetween, the density of the charged particles existing in the channel is changed. With the aid of this property, the current signal can be varied by changing the gate voltage. Hereinafter, a field-effect transistor and a single-electron transistor are both called simply a "transistor" when they are not necessary to be distinguished from each.

The currently known chemicals-sensing elements (sensors) using transistors are those utilizing the above-mentioned principles of transistors. As a specific example of sensors, the one described in Japanese Patent Laid-Open Publication (Kokai) No. Hei 10-260156 ("Patent Document 1") can be mentioned. Patent Document 1 discloses a sensor with construction that a substance which is capable of selectively reacting with detection targets is immobilized on the gate of the transistor. A change in the surface charge of the gate, induced by the reaction of the detection targets and the substance immobilized on the gate, varies the electric potential of the gate, thereby the density of the charged particles existing in the channel being changed. This change leads to the variation in the output signal from either the drain electrode or the source electrode of the transistor. Then the detection of a detection target can be made by reading that variation.

SUMMARY OF THE INVENTION

However, in order for a sensor like that to be used as an immune sensor using antigen-antibody reaction, extremely high detection sensitivity should be required. Therefore, it has not yet realized because of its technical limiting factors to the detection sensitivity.

The present invention has been made in view of such problems as mentioned above. The object of the invention is to provide a sensor that makes it possible to detect detection targets with high detection sensitivity.

The present inventors have found that a sensor for detecting detection targets using a transistor is able to detect the detection targets with high detection sensitivity, when the transistor comprises not only a source electrode, a drain electrode and a channel but also an interaction-sensing gate for immobilizing thereon a specific substance that is capable of selectively interacting with the detection targets and a gate applied a voltage thereto so as to detect the interaction by the change of the characteristic of the transistor, and achieved the present invention.

That is, a sensor of the present invention is a sensor for detecting detection targets, comprising a field-effect transistor having a substrate, a source electrode and a drain electrode provided on said substrate, and a channel forming a current path between said source electrode and said drain electrode; wherein said field-effect transistor comprises: an interaction-sensing gate for immobilizing thereon a specific substance that is capable of selectively interacting with the detection targets; and a gate applied a voltage thereto so as to detect the interaction by the change of the characteristic of said field-effect transistor. With this sensor, the interaction can be detected in a state where the transfer characteristic of the transistor shows the highest level in sensitivity. Thereby, the sensor can be highly sensitive.

Another sensor of the present invention is a sensor for detecting detection targets, comprising a single-electron transistor having a substrate, a source electrode and a drain electrode provided on said substrate, and a channel forming a current path between said source electrode and said e drain electrode; wherein said single-electron transistor comprises: an interaction-sensing gate for immobilizing thereon a specific substance that is capable of selectively interacting with the detection targets; and a gate applied a voltage thereto so as to detect the interaction by the change of the characteristic of said single-electron transistor (Claim 5). With this sensor, the interaction can be detected in a state where the transfer characteristic of the transistor shows the highest level in sensitivity. Thereby, the sensor can be highly sensitive.

As one preferred feature, said channel is formed with a nano tube structure. With this construction, the sensitivity of the sensor can be improved even further.

As another preferred feature, said nano tube structure is selected from the group consisting of a carbon nano tube, a boron nitride nano tube and a titania nano tube.

As still another preferred feature, the electric characteristic of said nano tube structure has the property like semiconductors.

As a further preferred feature, defects are introduced in said nano tube structure. With this construction, a quantum dot structure can be formed within the nano tube structure.

It is also preferred that the electric characteristic of said nano tube structure has the property like metals.

It is also preferred that said interaction-sensing gate is the other gate than said gate. With this construction, the transistor can be made up with simple construction.

It is also preferred that said other gate is any one of a top gate provided on the right side of said substrate, a side gate provided on the side of said channel on the surface of said substrate or a back gate provided on the back side of said substrate. With this construction, the detection can be operated easily.

It is also preferred that said channel is bridged between said source electrode and said drain electrode in the state where said channel is apart from said substrate. With this construction, the permittivity between the interaction-sensing gate and the channel gets lowered, which results in smaller capacitance of the interaction-sensing gate. Thus, the detection can be performed with high sensitivity.

It is also preferred that said channel is provided between said source electrode and said drain electrode in the state where said channel is bent at room temperature. With this construction, the risk of damage to the channel, which may be caused by a temperature change, can be reduced.

It is also preferred that said substrate is an insulated substrate.

It is also preferred that said channel is covered with an insulator.

With this construction, the current within the transistor can flow surely in the channel. Thereby, the detection can be performed steadily.

It is also preferred that a layer of low-permittivity insulating material is formed between said channel and said interaction-sensing gate. With this construction, electric charge variation caused by the interaction occurred at the interaction-sensing gate can be transmitted to the channel more efficiently. Thereby, the sensitivity of the sensor can be enhanced.

It is also preferred that a layer of high-permittivity insulating material is formed between said channel and said gate. With this construction, the transfer characteristic of the transistor can be modulated more efficiently using the gate voltage applied to the gate. Thereby, the sensitivity of the sensor can be enhanced.

It is also preferred that said specific substance is immobilized on said interaction-sensing gate.

A field-effect transistor of the present invention is a field-effect transistor used for a sensor to detect detection targets and having a substrate, a source electrode and a drain electrode provided on said substrate, and a channel forming a current path between said source electrode and said drain electrode; wherein said field-effect transistor comprises: an interaction-sensing gate for immobilizing thereon a specific substance that is capable of selectively interacting with the detection targets; and a gate applied a voltage thereto so as to detect the interaction by the change of the characteristic of said field-effect transistor.

Another field-effect transistor of the present invention is a field-effect transistor having a substrate, a gate, a source electrode and a drain electrode provided on said substrate, and a channel forming a current path between said source electrode and said drain electrode; wherein said channel is a nano tube structure bridged between said source electrode and said drain electrode in the state where said nano tube structure is apart from said substrate.

Still another field-effect transistor of the present invention is a field-effect transistor having a substrate, a gate, a source electrode and a drain electrode provided on said substrate, and a channel forming a current path between said source electrode and said drain electrode; wherein said channel is formed with a nano tube structure, and said nano tube structure is provided between said source electrode and said drain electrode in the state where said nano tube structure is bent at room temperature.

Still another field-effect transistor of the present invention is a field-effect transistor having a substrate, a gate, a source electrode and a drain electrode provided on said substrate, and a channel forming a current path between said source electrode and said drain electrode; wherein said channel is a nano tube structure, and said substrate is an insulated substrate.

Still another field-effect transistor of the present invention is a field-effect transistor having a substrate, a gate, a source electrode and a drain electrode provided on said substrate, and a channel forming a current path between said source electrode and said drain electrode; wherein said channel is a nano tube structure covered with an insulator.

A single-electron transistor of the present invention is a single-electron transistor used for a sensor to detect detection targets and having a substrate, a source electrode and a drain electrode provided on said substrate, and a channel forming a current path between said source electrode and said drain electrode; wherein said single-electron transistor comprises: an interaction-sensing gate for immobilizing thereon a specific substance that is capable of selectively interacting with the detection targets; and a gate applied a voltage thereto so as to detect the interaction by the change of the characteristic of said single-electron transistor.

Another single-electron transistor of the present invention is a single-electron transistor having a substrate, a gate, a source electrode and a drain electrode provided on said substrate, and a channel forming a current path between said source electrode and said drain electrode; wherein said channel is a nano tube structure bridged between said source electrode and said drain electrode in the state where said nano tube structure is apart from said substrate.

Still another single-electron transistor of the present invention is a single-electron transistor having a substrate, a gate, a source electrode and a drain electrode provided on said substrate, and a channel forming a current path between said source electrode and said drain electrode; wherein said channel is formed with a nano tube structure, and said nano tube structure is provided between said source electrode and said e drain electrode in the state where said nano tube structure is bent at room temperature.

Still another single-electron transistor of the present invention is a single-electron transistor having a substrate, a gate, a source electrode and a drain electrode provided on said substrate, and a channel forming a current path between said source electrode and said drain electrode; wherein said channel is a nano tube structure, and said substrate is an insulated substrate.

Still another single-electron transistor of the present invention is a single-electron transistor having a substrate, a gate, a source electrode and a drain electrode provided on said substrate, and a channel forming a current path between said source electrode and said drain electrode; wherein said channel is a nano tube structure covered with an insulator.

As one preferred feature, said nano tube structure is selected from the group consisting of a carbon nano tube, a boron nitride nano tube and a titania nano tube.

As another preferred feature, the electric characteristic of said nano tube structure provided with above-mentioned field-effect transistor has the property like semiconductors.

As still another preferred feature, defects are introduced in said nano tube structure provided with above-mentioned single-electron transistor. With this construction, quantum dot structure can be formed within the nano tube structure.

As still another preferred feature, the electric characteristic of said nano tube structure provided with above-mentioned single-electron transistor has the property like metals.

According to the sensor of the present invention, it is possible to detect detection targets with high detection sensitivity.

BRIEF DESCRIPTION OF THE DRAWINGS

FIG. 1 (*a*) is a perspective view and FIG. 1 (*b*) is a side view of the transistor, respectively.

FIG. 2 (*a*) is a perspective view and FIG. 2 (*b*) is a side view of the transistor, respectively.

FIG. 3 (*a*) is a perspective view and FIG. 3 (*b*) is a side view of the transistor, respectively.

FIG. 4 (*a*) is a perspective view and FIG. 4 (*b*) is a side view of the transistor, respectively.

FIG. 5 (*a*) is a perspective view and FIG. 5 (*b*) is a side view of the transistor, respectively.

FIG. 6 (*a*) is a perspective view and FIG. 6 (*b*) is a side view of the transistor, respectively.

FIG. 11 is a figure illustrating examples of the present invention.

FIG. 12 (*a*) to FIG. 12 (*c*) are figures illustrating examples of the present invention.

FIG. 17 is a graph illustrating a result of examples of the present invention.

Figure 1A:
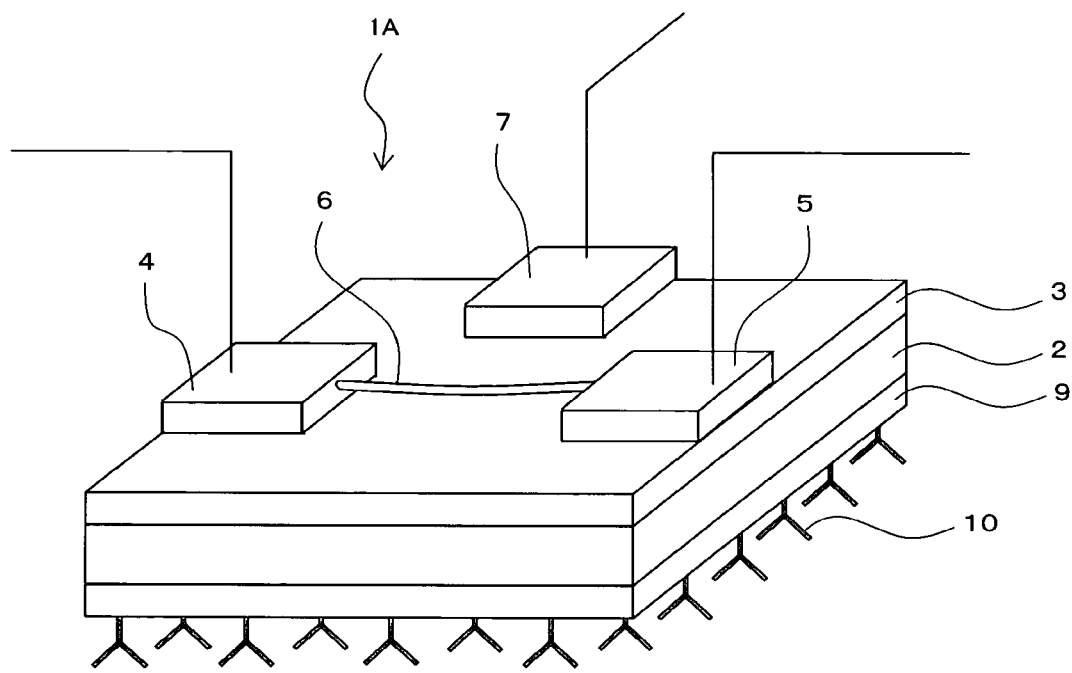
FIG. 1 (*a*) and FIG. 1 (*b*) illustrate sensors according to a first embodiment of the present invention.

EXPLANATION OF LETTERS OR NUMERALS 1A-1F transistor
2 substrate
3 law-permittivity layer
4 source electrode
5 drain electrode
6 channel
7 side gate
9 back gate (non voltage-applied and electrode-construction type member)
10 antibody
11 high-permittivity layer
12 back gate
13 insulating membrane
14 top gate (non voltage-applied and electrode-construction type member)
15 side gate (non voltage-applied and electrode-construction type member)
16 photoresist (channel protecting layer)
17 catalyst
18 CVD (chemical vapor deposition) furnace
19 carbon nano tube
20 spacer layer (insulating layer)
21 insulator

DETAILED DESCRIPTION OF THE INVENTION

In the following, embodiments of the present invention will be described. The present invention is not restricted to the following embodiments, but any modification can be made without departing from the scope of the present invention. In the following first to fifth embodiments, the word "transistor" is used to mean both the field-effect transistor and the single-electron transistor without being distinguished each other. Also, in the following embodiments, components that are substantially the same have the same reference letters as in the other embodiments.

First Embodiment

Figure 1B:
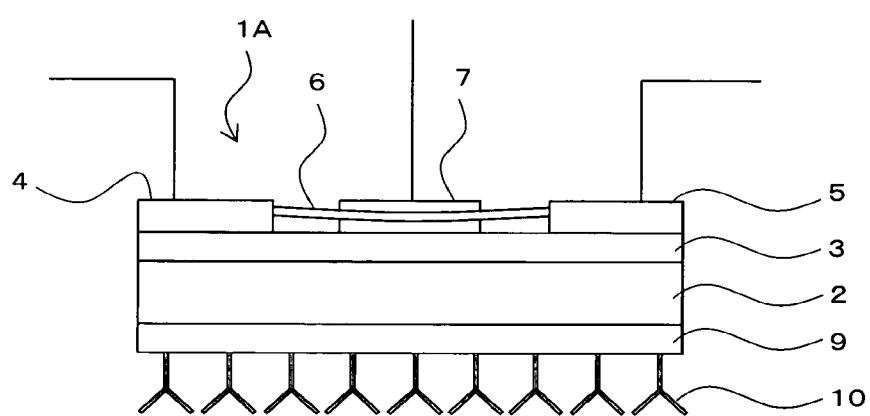

FIG. 1 (*a*) and FIG. 1 (*b*) illustrate sensors according to a first embodiment of the present invention. As shown in FIG. 1 (*a*), the substrate 2 of the transistor 1A is made of insulating material. On the upside (upper side in the Figs.) of the entire substrate, the silicon oxide layer of insulating and low-permittivity material (hereinafter, called "low-permittivity layer," if necessary) 3 is formed. On the right side of the low-permittivity layer 3, the source electrode 4 and the drain electrode 5, formed of gold, are placed, between which the channel 6 formed with a carbon nano tube is bridged.

The channel 6 is bridged between the source electrode 4 and the drain electrode 5 as if it were a bridge that connects the source electrode 4 and the drain electrode 5. Thereby it is apart from the low-permittivity layer 3 and the channel 6 is fixed to the transistor 1A at its two connecting points with the source electrode 4 and the drain electrode 5. The other portion of the channel 6 is in a state of being suspended in the air. Furthermore, as shown in FIG. 1 (*b*), the channel 6 is bridged in a state of being bent at a predetermined angle. The channel 6 is bent at a predetermined angle to the extent that the compressive or tensile stress exerted upon the channel 6 can be absorbed, for example when the distance between the source electrode 4 and the drain electrode 5 is varied by the deformation of the substrate 2 by a temperature change. Usually, the channel 6 is set up to bent at a predetermined angle around the temperatures at which the sensor is used. Thereby it is able to absorb the stress caused by the temperature change in the neighborhood of the temperatures at which the sensor is used. But, in this embodiment, the channel 6 is set up to bent at a predetermined angle at room temperature.

At the opposed position of the channel 6 on the low-permittivity layer 3, the side gate 7, formed of gold, is placed. The side gate 7 is placed for applying a gate voltage to the channel 6. The source electrode 4, the drain electrode 5 and the side gate 7 are connected to an external power source, not shown in Figs., and are set up to be placed with a voltage by the external power source. Moreover, the currents through the source electrode 4, the drain electrode 5 and the side gate 7 and the voltages applied to them are measured by a measuring instrument, not shown in Figs., respectively.

The transistor 1A of this embodiment further comprises the back gate (the other gate) 9, as an interaction-sensing gate, formed of gold on the back side (lower side in the Figs.) of the entire substrate 2, or the opposite side to the low-permittivity layer 3. A specific substance (an antibody in the present embodiment) 10 that is capable of selectively interacting with the targets to be detected by the sensor of the present embodiment is immobilized on the back gate 9.

The back gate 9 is set up not to be applied any voltages from outside.

With the above-mentioned construction of the sensor of the present embodiment, before or during the measurement, the most suitable gate voltage that the transfer characteristic of the transistor 1A shows the highest sensitivity will be tested to be found, by adjusting the gate voltage applied to the side gate 7. When the most suitable gate voltage is found, it will be set as the gate voltage applied to the side gate 7.

After that, maintaining the gate voltage to be the most suitable gate voltage or in the vicinity thereof, a sample containing targets to be detected is made to interact with the specific substance. The vicinity of the most suitable gate voltage means the range such that the change of the characteristic of the transistor is expected to reach the sufficient level on the detection of the detection targets. If the sample contains any detection targets, the electric potential of the back gate 9 will be changed by the interaction between the specific substance and the detection target, which leads to the change in the characteristic value of the transistor, such as the current value of the current between the source electrode and the drain electrode, the threshold voltage or the gradient of the drain voltage to the gate voltage, or in the characteristic value peculiar to single-electron transistors, such as the threshold of Coulomb Oscillation, the Coulomb Oscillation period, the threshold of Coulomb Diamond or the Coulomb Diamond period. By detecting this change, the interaction of the detection targets with the specific substance can be detected. Furthermore, this detection indicates the existence of the detection targets in the sample.

According to the sensor of the present embodiment, as mentioned above, the transistor 1A can be set, using the side gate 7, in such a state that the transfer characteristic thereof shows the highest level in sensitivity, or that the transconductance thereof reaches the highest level. Thus, the influence given to the density change of the charged particles in the channel 6 by the change in the gate voltage, caused by the interaction between the specific substance and the detection targets, can be maximized. As a result, the interaction between the specific substance and the detection targets can be measured as a large range of change in the characteristic of the transistor 1A. Consequently, the sensor according to the present embodiment can be set to be highly sensitive by amplifying the change in the characteristic of the transistor caused by the interaction between the specific substance and the detection targets.

In addition, because a carbon nano tube, a kind of a nano tube structure, is used as the channel 6, the detection targets can be detected with higher sensitivity. Generally, the limit of the detection sensitivity of a sensor using a transistor relates to the capacitance of the gate of the transistor (hereinafter, called "gate capacitance," if necessary). The smaller the gate capacitance is, the wider range of the change in the gate electric potential, which indicates the change in the surface electric charge of the gate, can be detected and thus the detection sensitivity of the sensor can be improved. Because the gate capacitance is proportional to the product of the length of the channel L and the width W, or L×W, it is efficient to make the channel to be minute in order to reduce the gate capacitance. For these reasons, with a nano tube structure of this embodiment, which is extremely minute, detection targets can be detected with extremely high sensitivity.

Also, because the back gate 9 is used as an interaction-sensing gate and antibody is immobilized on the back gate, high sensitivity detection can be performed with a simple construction. More specifically, because the back gate 9 is placed on the back side of the substrate 1A, the detection can be operated easily.

Also, because the channel 6 is bridged between the source electrode 4 and the drain electrode 5 in a state of being bent, the risk of damage to the channel 6, induced by its deformation by temperature changes, can be reduced.

Also, because the substrate 2 is an insulating substrate, the interaction at the back gate 9 can be surely detected.

Also, because the low-permittivity layer 3 is formed between the channel 6 and the back gate (interaction-sensing gate) 9, the change in the surface charge caused by the interaction at the back gate 9 is transmitted more efficiently as a change of the electric charge density in the channel 6 and make itself shown as a large change in the characteristic of the transistor 1A. Consequently, the sensitivity of the sensor of the present embodiment is able to be highly enhanced.

Also, the use of the sensor of the present embodiment makes it possible to real-time measure, thereby the monitoring of the interaction between materials being realized.

Also, conventional detection equipment using immunity reaction or the like based on the other principles of detection, using markers like radio immuno assay and chemiluminescence immuno assay, has been quite satisfactory in its detection sensitivity. However, it requires specialized facilities and equipment systems and the measurement using them should be taken at the inspection center or the inspection room in the hospital by medical engineers who are the specialists in the field. Thus, doctors in private practice can not obtain the result of detection quickly, because they have to perform inspections by ordering with outside inspection centers. In addition, because they needs long reaction time, few of them can be used in emergency inspections. The reason of the above-mentioned problems is that complicated operations like washing are required in the reaction process owing to the use of markers in the present immune measurement.

Further, though non-marker method immune sensors based on various principles such as surface plasmon resonance (SPR) have been developed, they have all been used as equipment for researches so not yet in practical use, for the lack of sufficient sensitivity fit for clinical-trial use. Also this immune sensor has a problem that the whole equipment is very upsized by the use of optical detection method.

However, the sensor of the present embodiment can achieve the advantages such as downsizing of the sensor, the rapidity of detection, the ease with operation, and so on.

Second Embodiment

Figure 2A:
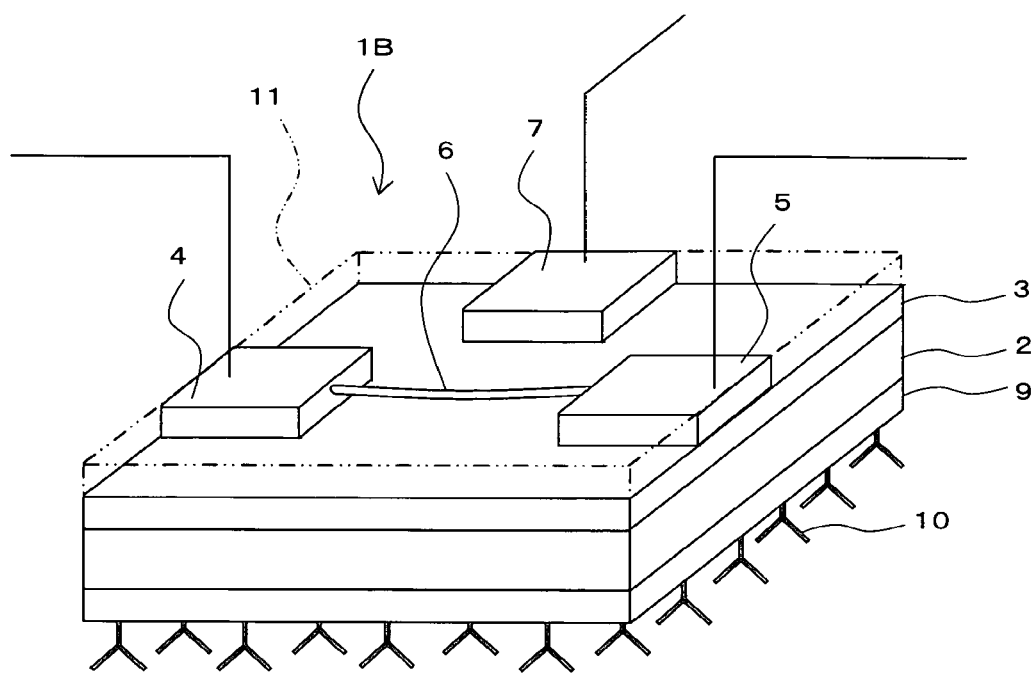
FIG. 2 (*a*) and FIG. 2 (*b*) illustrate sensors according to a second embodiment of the present invention.
Figure 2B:
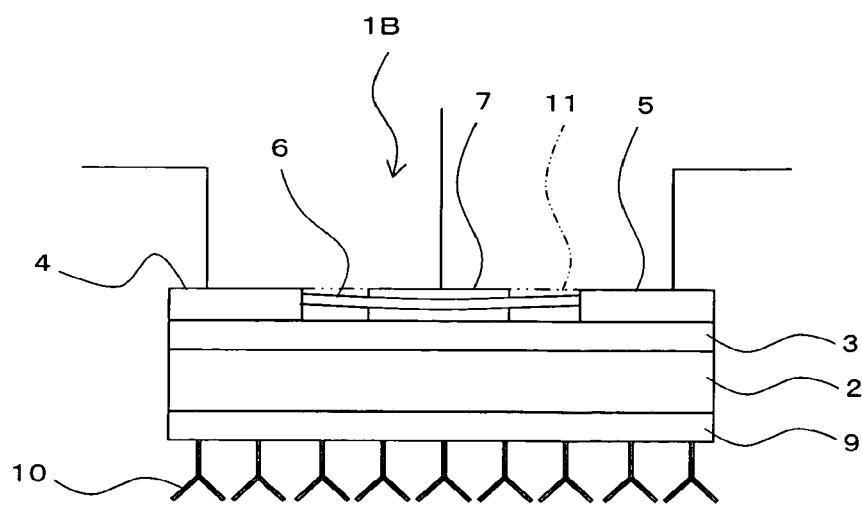

FIG. 2 (a) and FIG. 2 (b) illustrate sensors according to a second embodiment of the present invention. As shown in FIG. 2 (a), the transistor 1B constructing the sensor of the second embodiment of the present invention has similar structure to the transistor 1A described in the first embodiment.

The transistor 1B of the present embodiment further comprises the photosensitive resin layer of insulating and high-permittivity material (hereinafter, called "high-permittivity layer," if necessary) 11 is formed on the upside of the entire low-permittivity layer 3. The high-permittivity layer 11 is formed to cover the whole channel 6, the lateral sides of the source electrode 4, the drain electrode 5 and the side gate 7 but not to cover the upsides (upper sides in Figs.) of the source electrode 4, the drain electrode 5 and the side gate 7. The high-permittivity layer 11 is shown by chain double-dashed line in FIG. 2 (a) and FIG. 2 (b).

Because the sensor of the present embodiment is constructed as mentioned above, similar to the sensor of the first embodiment, it can be set in such a state that the transfer characteristic of the transistor 1B shows the highest level in sensitivity. Then, this makes it possible to measure the interaction between the specific substance and the detection targets as a wide range of change in the characteristic of the transistor 1B. Consequently, the sensor sensitivity of the present embodiment can be improved.

The following advantageous effects can be taken similar to the first embodiment. That is, because a carbon nano tube is used as a channel 6, the sensor can have higher sensitivity. Also, because the back gate 9 is used as an interaction-sensing gate, high sensitivity detection can be performed with simple construction and by simple operation. Also, because the substrate 2 is an insulating substrate, the interaction between the detection targets and the specific substance can be surely detected. Also, because the low-permittivity layer 3 is formed between the channel 6 and the back gate 9, the change in the surface charge caused by the interaction at the back gate 9 is transmitted to the channel 6 more efficiently, thereby the sensor sensitivity of the present embodiment can be further improved. Also, because the channel 6 is bent, the damage induced by the variation of length, caused by temperature changes or the like, can be prevented. In this embodiment, though the high-permittivity layer 11 is filled around the channel 6, photosensitive resin (photoresist), which consists of the high-permittivity layer 11, is formed of material that is soft enough to allow deformation of the channel 6, thereby the damage can be prevented as mentioned above.

Further, in this embodiment, because the high-permittivity layer 11, a layer of high-permittivity and insulating material, is formed between the channel 6 and the side gate 7, the transfer characteristic of the transistor 1B can be more efficiently modulated by applying the gate voltage of the side date 7. Consequently, the sensitivity of the sensor is able to be further improved.

Also, because the channel 6 is covered with the insulating and high-permittivity layer 11, leaking of the charged particles in the channel 6 to the outside thereof and intrusion of the charged particles to the channel 6 from outside of the channel 6, other than from the source electrode or the drain electrode, are able to be prevented. This results in that the interaction between the specific substance and detection targets can be detected steadily.

Also, the use of the sensor of the present embodiment makes it possible to real-time measure, thereby the monitoring of interaction between materials being realized. Further, it can be integrated easily, thereby a phenomenon of interaction between materials happened simultaneously in many places can be measured at a time.

Also, the sensor of the present embodiment can achieve the advantages such as downsizing of the sensor, the rapidity of detection, the ease with operation, and so on.

Third Embodiment

Figure 3A:
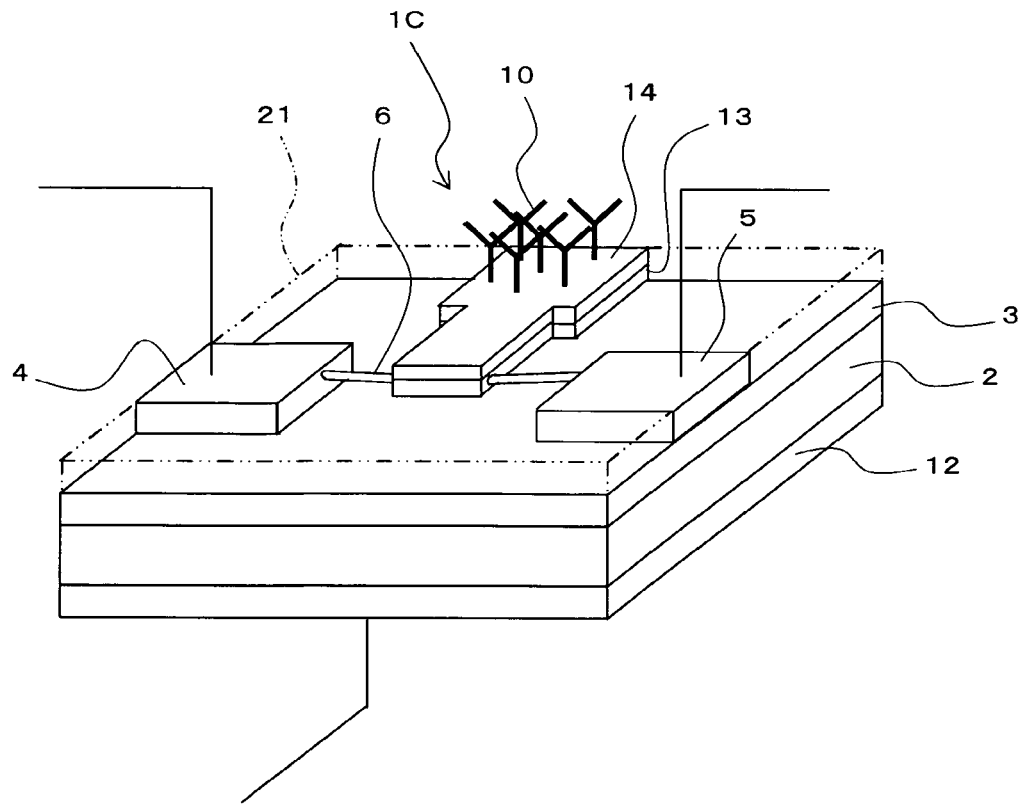
FIG. 3 (*a*) and FIG. 3 (*b*) illustrate sensors according to a third embodiment of the present invention.
Figure 3B:
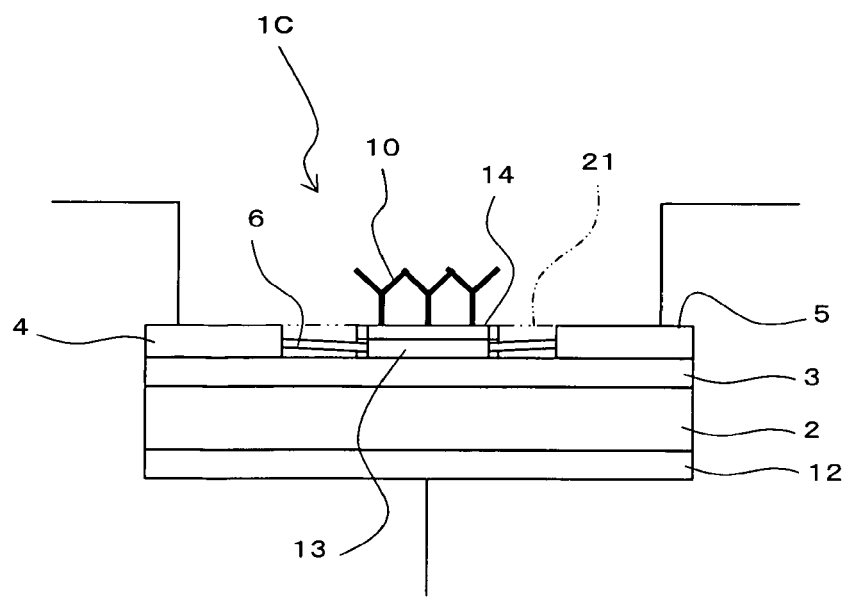

FIG. 3 (*a*) and FIG. 3 (*b*) illustrate sensors according to the third embodiment of the present invention. As shown in FIG. 3 (*a*), the transistor 1C constructing the sensors according to this embodiment, similar to the first embodiment, comprises the substrate 2 fabricated with insulating material, the insulating and low-permittivity layer 3, the source electrode 4 and the drain electrode 5. The source electrode 4 and the drain electrode 5 are formed with gold. The channel 6 formed with a carbon nano tube is bridged between the source electrode 4 and the drain electrode 5.

The back gate 12 for applying a gate voltage to the transistor 1C is formed on the back side of entire substrate 2. The back gate 12 is connected to a power supply, not shown in Figs., which applies a voltage to the back gate 12. The voltage placed to the back gate 12 is able to be measured with a measuring instrument, not shown in Figs.

The membrane fabricated with silicon oxide (insulating membrane) 13 is formed, on the right side of the low-permittivity layer 3, from the middle of the channel 6 to the edge of the layer 3 in the depth direction in Figs.

The channel 6 penetrates the insulating membrane 13 sideways. In other words, the portion around the middle of the channel 6 is covered with insulating membrane 13.

On the upper side of the insulating membrane 13, the top gate 14 is formed of gold as an interaction-sensing gate. Thus, the top gate 14 is placed on the low-permittivity layer 3 with the insulating membrane 13 between them. The top gate 14 is constructed not to be applied with any voltage from outside. Further, the antibody 10 or the specific material is immobilized on the right side of the top gate 14.

The insulator 21 is formed on the right side of the entire low-permittivity layer 3. The insulator 21 is formed to cover the portions of the channel 6 uncovered with insulating membrane 13, the lateral sides of the source electrode 4, the drain electrode 5, the insulating membrane 13 and the top gate 14, but not to cover the upsides of the source electrode 4, the drain electrode 5 and the top gate 14. The insulator 21 is shown by chain double-dashed line in FIG. 3 (*a*) and FIG. 3 (*b*).

Because the sensor of the third embodiment of the present invention is constructed as mentioned above, similar to the sensor of the first embodiment, it can be set in such a state that the transfer characteristic of the transistor 1C shows the highest level in sensitivity. Then, this makes it possible to measure the interaction between the specific substance and the detection targets as a wide range of change in the characteristic of the transistor 1C. Consequently, the sensor sensitivity of the present embodiment can be improved.

Also, similar to the first embodiment, because a carbon nano tube is used for the channel 6, the sensor can have higher sensitivity. Also, because the substrate 2 is an insulating substrate, the interaction between the detection targets and the specific substance can be surely detected.

Also, because the top gate 14 is used as an interaction-sensing gate, high sensitivity detection can be performed with simple construction and by simple operation.

Also, because the low-permittivity insulating membrane 13 is formed between the channel 6 and the top gate 14, the change in the surface charge caused by the interaction at the top gate 14 is transmitted to the channel 6 more efficiently; thereby the sensor sensitivity of the present embodiment can be further improved.

Also, because the channel 6 is covered with the insulator 21, leaking of the charged particles in the channel 6 to the outside thereof and intrusion of the charged particles to the channel 6 from outside of the channel 6, other than from the source electrode or the drain electrode, are able to be prevented. This results in that the interaction between the specific substance and detection targets can be detected steadily.

Also, the use of the sensor of the present embodiment makes it possible to measure real-time, thereby to be realized the monitoring of interaction between materials. Further, it can be integrated easily, thereby a phenomenon of interaction between materials happened simultaneously in many places can be measured at a time.

Also, the sensor of the present embodiment can achieve the advantages such as downsizing of the sensor, the rapidity of detection, the ease with operation, and so on.

Fourth Embodiment

Figure 4A:
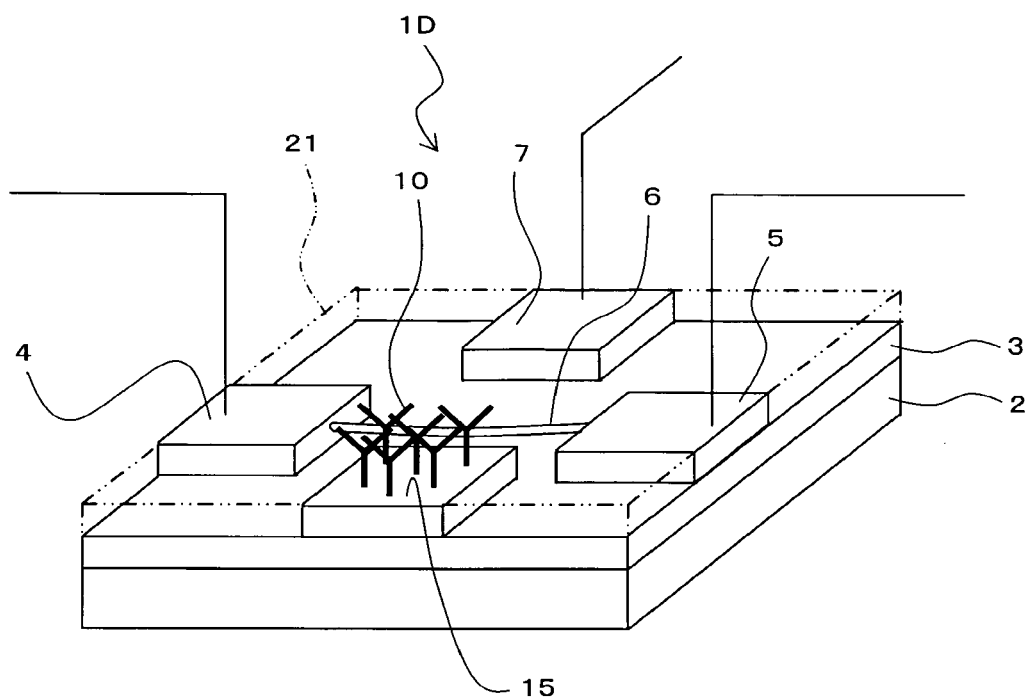
FIG. 4 (*a*) and FIG. 4 (*b*) illustrate sensors according to a fourth embodiment of the present invention.
Figure 4B:
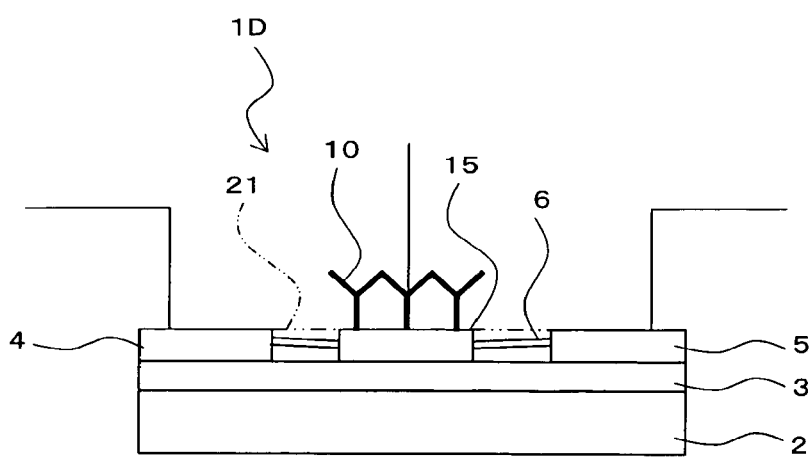

FIG. 4 (a) and FIG. 4 (b) illustrate sensors according to a fourth embodiment of the present invention. As shown in FIG. 4 (a), the transistor 1D constructing the sensors according to this embodiment, similar to the first embodiment, comprises the substrate 2 formed of insulating material, the insulating and low-permittivity layer 3, the source electrode 4 and the drain electrode 5. The source electrode 4 and the drain electrode 5 are formed of gold. The channel 6 formed with a carbon nano tube is bridged between the source electrode 4 and the drain electrode 5. And the transistor 1D also comprises the side gate 7.

The transistor 1D of the present embodiment further comprises the side gate 15 as an interaction-sensing gate on the opposite-side edge of low-permittivity layer 3 to the side gate 7, on the right side of which antibodies 10 are immobilized. The side gate 15 is constructed that in such a state that any voltages are not applied from the outside.

As shown in FIG. 4 (b), the transistor 1D of the present embodiment also comprises the insulator 21 provided on the upside of the entire low-permittivity layer 3. The insulator 21 is formed to cover the whole channel 6, the lateral sides of the source electrode 4, the drain electrode 5 and the side gate 7, 15 but not to cover the upsides (upper sides in Figs.) of the source electrode 4, the drain electrode 5 and the side gate 7, 15. The insulator 21 is shown by chain double-dashed line in FIG. 4 (a) and FIG. 4 (b).

Because the sensor of the present embodiment is constructed as mentioned above, similar to the sensor of the first embodiment, it can be set in such a state that the transfer characteristic of the transistor 1D shows the highest level in sensitivity. Then, this makes it possible to measure the interaction between the specific substance and the detection targets as a wide range of change in the characteristic of the transistor 1D. Consequently, the sensor sensitivity of the present embodiment can be improved.

The following advantageous effects can be taken similar to the first embodiment. That is, because a carbon nano tube is used as a channel 6, the sensor can have higher sensitivity. Also, because the side gate 15 is used as an interaction-sensing gate, high sensitivity detection can be performed with simple construction. Also, because the substrate 2 is an insulating substrate, the interaction between the detection targets and the specific substance can be surely detected.

Also, because the channel 6 is covered with the insulating insulator 21, leaking of the charged particles in the channel 6 to the outside thereof and intrusion of the charged particles to the channel 6 from outside of the channel 6, other than from the source electrode 4 or the drain electrode 5, are able to be prevented. This results in that the interaction between the specific substance and detection targets can be detected steadily.

Also, the use of the sensor of the present embodiment makes it possible to measure real-time, thereby to be realized the monitoring of interaction between materials. Further, it can be integrated easily, thereby a phenomenon of interaction between materials happened simultaneously in many places can be measured at a time.

Also, the sensor of the present embodiment can achieve the advantages such as downsizing of the sensor, the rapidity of detection, the ease with operation, and so on.

Fifth Embodiment

Figure 5A:
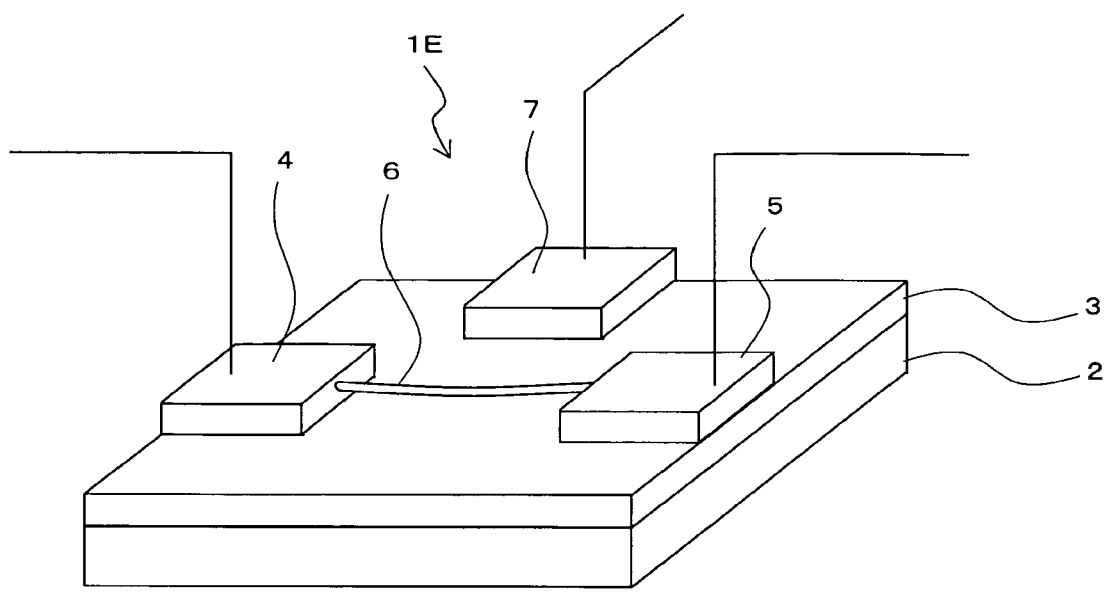
FIG. 5 (*a*) and FIG. 5 (*b*) illustrate sensors according to a fifth embodiment of the present invention.
Figure 5B:
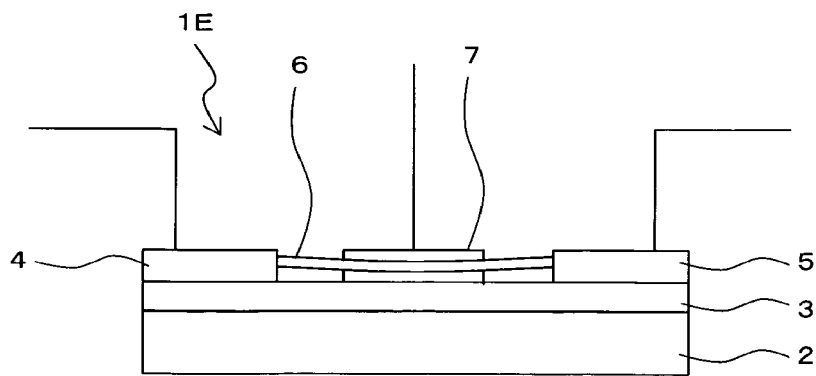

FIG. 5 (a) and FIG. 5 (b) illustrate sensors according to the fifth embodiment of the present invention.

The transistor 1E of the fifth embodiment of the present invention, as shown in FIG. 5 (a) and FIG. 5 (b), has similar construction to the transistor 1A of the first embodiment, other than that it does not comprise the back gate 9 and the antibodies 10.

That is, as shown in FIG. 5 (a), the substrate 2 of the transistor 1A is fabricated with insulating material. On the upside (upper side in the Figs.) of the entire substrate 2, the silicon oxide layer (low-permittivity layer) 3 of insulating and low-permittivity material is formed. On the right side of the low-permittivity layer 3, the source electrode 4 and the drain electrode 5, formed with gold, are placed, between which the channel 6 formed with a carbon nano tube is bridged.

The channel 6 is bridged between the source electrode 4 and the drain electrode 5 as if it were a bridge that connects the source electrode 4 and the drain electrode 5, thereby it is apart from the low-permittivity layer 3. Thus, the channel 6 is fixed to the transistor 1A at its two connecting points with the source electrode 4 and the drain electrode 5. The other portion of the channel 6 is in a state of being suspended in the air. Furthermore, as shown in FIG. 5 (b), the channel 6 is bridged in a state of being bent at a predetermined angle. The channel 6 is bent at a predetermined angle to the extent that the compressive or tensile stress exerted upon the channel 6 can be absorbed, for example when the distance between the source electrode 4 and the drain electrode 5 is varied with deformation of the substrate 2 by a temperature change. Usually, the channel 6 is adjusted to bent at a predetermined angle around the temperatures at which the sensor is used, thereby it is able to absorb the stress caused by the temperature change in the neighborhood of the temperatures at which the sensor is used. But, in this embodiment, the channel 6 is set up to bent at a predetermined angle at room temperature.

At the opposed position of the channel 6 on the low-permittivity layer 3, the side gate 7, formed with gold, is placed. The side gate 7 is placed for applying a gate voltage to the channel 6. The source electrode 4, the drain electrode 5 and the side gate 7 are connected to an external power source, not shown in Figs., and are set up to be placed with a voltage by the external power source.

Because the transistor 1E of the present embodiment is constructed as mentioned above, owing to the fact that the channel 6 is bridged between the source electrode 4 and the drain electrode 5 in a state of being bent, the risk of damage to the channel 6, induced by its deformation by temperature changes, can be reduced even with a temperature change when it is used for detection or kept unused.

Also, because the substrate 2 of the present embodiment is an insulating substrate, the permittivity of the substrate 2 can get lowered, which leads to the reduction in the gate capacitance, thereby the sensitivity of the transistor 1E can be enhanced.

Sixth Embodiment

Figure 6A:
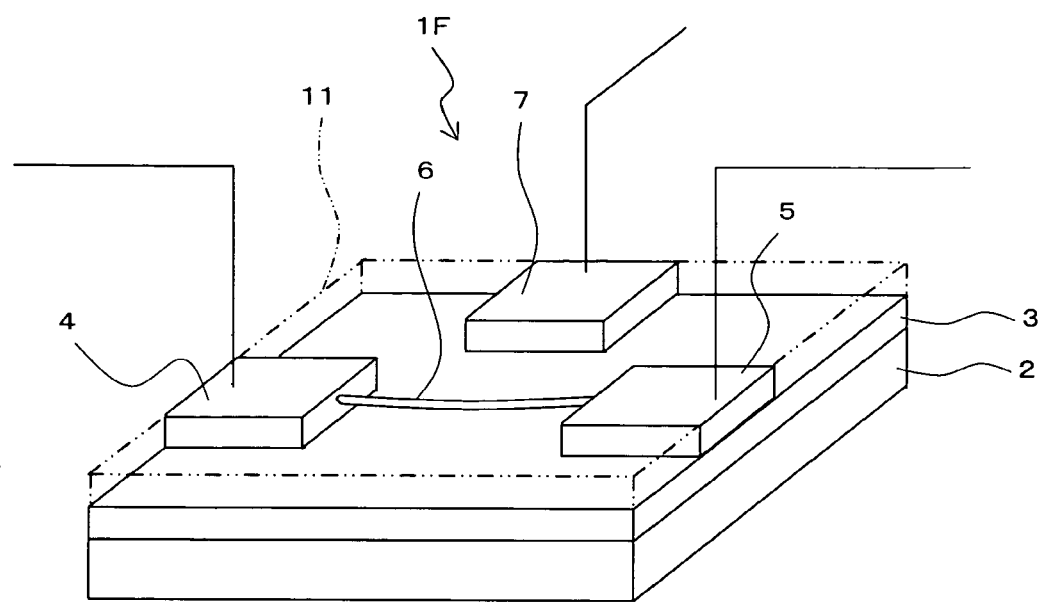
FIG. 6 (*a*) and FIG. 6 (*b*) illustrate sensors according to a sixth embodiment of the present invention.
Figure 6B:
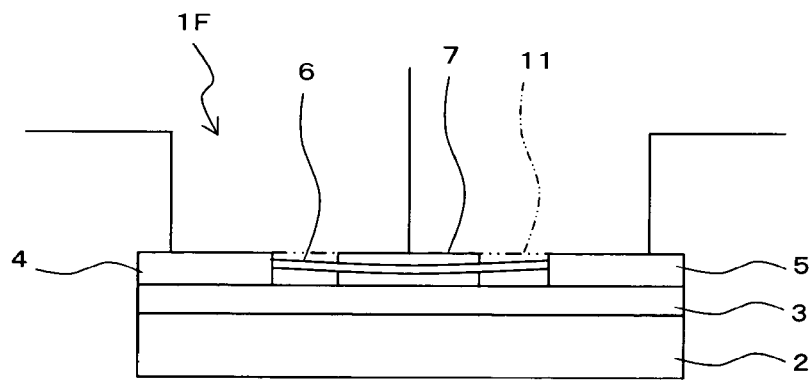
Figure 7A:
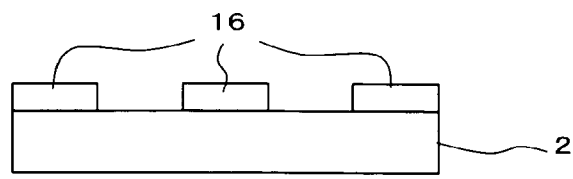
FIG. 7 (*a*) to FIG. 7 (*d*) are figures illustrating an example of producting method of a transistor according to an embodiment of the present invention.
Figure 7B:
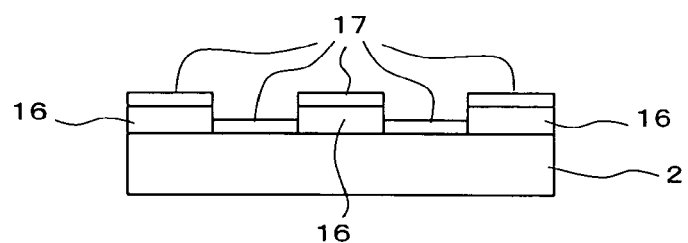
Figure 7C:
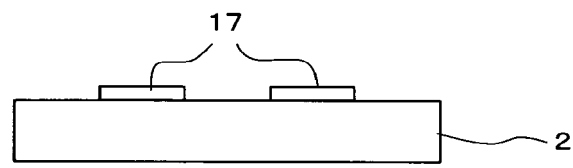
Figure 7D:
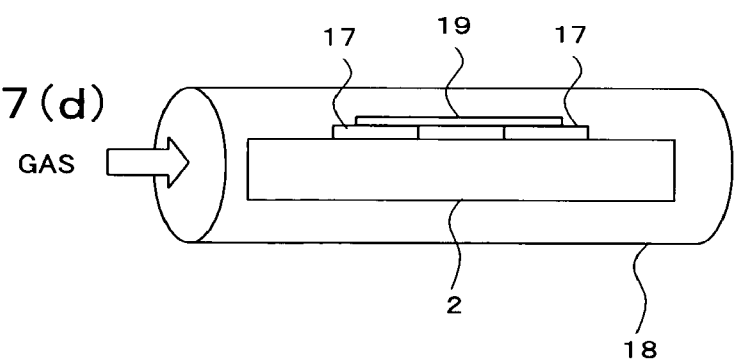

FIG. 6 (a) and FIG. 6 (b) illustrate sensors according to the sixth embodiment of the present invention.

The transistor 1F of the sixth embodiment of the present invention, as shown in FIG. 6 (a) and FIG. 6 (b), has similar construction to the transistor 1B of the second embodiment, other than that it does not comprise the back gate 9 and the antibodies 10.

That is, as shown in FIG. 6 (a), the transistor 1F constructing the sensor of the sixth embodiment of the present invention has similar structure to the transistor 1E described in the fifth embodiment.

The transistor 1F of the present embodiment further comprises the photosensitive resin layer of insulating and high-permittivity material (high-permittivity layer) 11 is formed on the upside of the entire low-permittivity layer 3. The high-permittivity layer 11 is formed to cover the whole channel 6, the lateral sides of the source electrode 4, the drain electrode 5 and the side gate 7 but not to cover the upsides (upper sides in Figs.) of the source electrode 4, the drain electrode 5 and the side gate 7. The high-permittivity layer 11 is shown by chain double-dashed line in FIG. 6 (a) and FIG. 6 (b).

The sensor of the present embodiment is constructed as above-mentioned. Thus, in this embodiment, because the high-permittivity layer 11, a layer of high-permittivity and insulating material, is formed between the channel 6 and the side gate 7, the transfer characteristic of the transistor 1E can be more efficiently modulated by applying the gate voltage of the side date 7.

Also, because the channel 6 is covered with the insulating and high-permittivity layer 11, leaking of the charged particles in the channel 6 to the outside thereof and intrusion of the charged particles to the channel 6 from outside of the channel 6, other than from the source electrode 4 or the drain electrode 5, are able to be prevented. This results in that the behavior of the transistor 1E can be stabled.

Others

Up to this point, though the present invention has been explained as the forms of the first to sixth embodiments, the present invention is not limited to the above embodiments but also can be carried out with various modifications.

For example, above embodiments may be carried out in combination arbitrarily.

For another example, the source electrode, drain electrode, gate, channel and interaction-sensing gate may be provided plurally.

For still another example, in the above embodiments, though the construction of the sensor is that the transistors are exposed, the transistor may be installed inside of an appropriate housing or installed on the other equipment.

For still another example, though in the above embodiments the specific substances are immobilized on the sensors, the sensor may not be immobilized with the specific substance thereon in the stage of manufacture or shipment, but the specific substance may be immobilized by a user. That is, it is to be understood that the embodiments of the sensors of the present invention may include those that are not immobilized with specific substances thereon.

For still another example, though the top gate, side gate and back gate have been used as an interaction-sensing gate in the above embodiments, it is needless to say that any other gate, as well as any other members than gates, may be used as an interaction-sensing gate.

For still another example, though the channel 6 has been constructed to be bent in the above embodiments, of course it may not be bent but be straight.

For still another example, though the channel 6 has been bridged between the source electrode 4 and the drain electrode 5 in the above embodiments, it may be provided being touched with the substrate 2 or the low-permittivity layer 3, for example. As far as the channel 6 is bent, even in a state where it is touched with the substrate 2 or the low-permittivity layer 3, the risk of damage to it caused by temperature changes can be reduced.

For still another example, a voltage can be applied on the interaction-sensing gate.

Components

In the following, components in the above embodiments are described particularly.

As mentioned above, the word "transistor" in the above embodiments means either the field-effect transistor or the single-electron transistor.

A field-effect transistor and a single-electron transistor are the same in their basic structure, while the channels, which form current paths, of them are different. More specifically, the channel of the single-electron transistor has a quantum dot structure and the channel of the field-effect transistor does not. Thus, they can be distinguished in the form of their construction by the existence of a quantum dot structure.

Substrate

For a substrate (indicated by the numeral reference 2 in the above embodiments), those made of any materials may be used as far as they are insulating substrates or insulated semiconductor substrates, without any other restriction. But it is preferred to be insulating substrates or substrates with its surfaces covered with the material used for the insulating substrates, when they are used in sensors. When an insulating substrate is used, floating capacitance can be reduced because the permittivity of an insulating substrate is lower compared to the semiconductor substrate. Thereby, the detection sensitivity to detect the interaction with can be improved when a back gate is used as the interaction-sensing gate.

An insulating substrate is a substrate formed with an insulator, which means an electric insulator as far as it is not specifically mentioned in the present specification. Examples of the insulator that forms the insulating substrate are silicon oxide, silicon nitride, aluminum oxide, titanium oxide, calcium fluoride, acrylic resin, polyimide resin, Teflon (registered trademark), etc. These examples may used in any kinds of combination with any percentage of each.

A semiconductor substrate is a substrate formed with semiconductors. Examples of the semiconductor that forms the semiconductor substrate are silicon, gallium arsenide, gallium nitride, zinc oxide, indium phosphide, silicon carbide, etc. These examples may used in any kinds of combination with any percentage of each.

When an insulating membrane is formed on the semiconductor substrate in order to insulate it, examples of the insulator that forms the insulating membrane are the same as those used for the insulator that forms the above-mentioned insulating substrate. In this case, the semiconductor substrate can also work as a gate described below.

The shape of the substrate is not limited particularly. But it is usually manufactured in the form of a plate. The size of the substrate is not restricted, either. But it is preferred to be more than 100 micrometers so as to maintain its mechanical strength.

Source Electrode and Drain Electrode

For a source electrode (indicated by the numeral reference 4 in the above embodiments), there is no restrictions as far as it is an electrode that can supply carriers of the above-mentioned transistors. For a drain electrode (indicated by the numeral reference 5 in the above embodiments), there is no restrictions either as far as it is an electrode that can receive carriers of the above-mentioned transistors.

The source electrode as well as the drain electrode may be formed of any electric conductors. Examples thereof are gold, platinum, titanium, titanium carbide, tungsten, aluminum, molybdenum, chromium, tungsten silicide, tungsten nitride, polycrystal silicon, or the like. These examples may used in any kinds of combination with any percentage of each.

Gate

For gates (indicated by the numeral reference 7, 12 in the above embodiments), any types of materials may be used as far as they are able to control the density of the charged particles in the channel, without any other restriction. A gate is usually constructed to have a conductor insulated from the channel and generally consisted of a conductor and an insulator.

Examples of conductors forming gates are gold, platinum, titanium, titanium carbide, tungsten, tungsten silicide, tungsten nitride, aluminum, molybdenum, chromium, polycrystal silicon, etc. These examples may used in any kinds of combination with any percentage of each.

The location of the gate has no restrictions as far as the gate voltage can be applied to the channel. For example, it may be installed as a top gate which is upward to the substrate, as a side gate on the same surface as the channel of the substrate or as a back gate on the back side of the substrate.

In these kinds of gates, the top gate and the side gate may be formed on the surface of the channel with an insulating membrane between them. For this insulating membrane, there is no restriction as far as it is an insulating material, of which examples are inorganic materials like silicon oxide, silicon nitride, aluminum oxide, titanium oxide, calcium fluoride, and polymer materials like acrylic resin, epoxy resin, polyimide, Teflon (registered trademark), etc.

Interaction-Sensing Gate

For an interaction-sensing gate (indicated by the numeral references 9, 14 and 15 in the above embodiments), any types of members may be used as far as they are able to immobilize specific substances thereon that are capable of selectively interacting with the detection targets. Thus, the interaction-sensing gate can be called an immobilizing member. In another aspect, the interaction-sensing gate can be called a non voltage-applied type immobilizing member because it is preferred not to be applied with a voltage from outside. In still another aspect, conductors, semiconductors or even insulators may be used as an interaction-sensing gate for example. But usually conductors are used for the interaction-sensing gate, as in the case of the source electrode and the drain electrode. Thus, the interaction-sensing gate can be called an electrode-construction type member. Further, to consider that it is not applied with a voltage, too, it can also be called a non voltage-applied and electrode-construction type member. Examples of conductors forming the interaction-sensing gate are gold, platinum, titanium, titanium carbide, tungsten, tungsten silicide, tungsten nitride, aluminum, molybdenum, chromium, polycrystal silicon, etc. These examples may used in any kinds of combination with any percentage of each.

Also, it is preferred that the gate without any gate voltage application in the transistor is used as an interaction-sensing gate. More specifically, the top gate, side gate or back gate can be selected preferably. Among the three of them, especially the top gate or back gate can be selected preferably. With the use of the top gate as an interaction-sensing gate, the distance to the channel is generally smaller compared to two other gates and thus the sensitivity of the sensor can be enhanced. If the back gate is used as an interaction-sensing gate, the specific substance can be immobilized on the interaction-sensing gate easily.

Channel

The channel (indicated by the numeral reference 6 in the above embodiments) may form a current path between the source electrode and the drain electrode. Any known types of channels can be used, if necessary.

The channel is preferred to be passivated or protected with the cover of insulating materials. Any insulating materials can be used as the insulating cover. Examples of them are polymer materials like photoresist (photosensitive resin), acrylic resin, epoxy resin, polyimide, Teflon (registered trademark), and self-organizing membrane like aminopropylethoxysilane, lubricants like PER-fluoropolyether, Fonbrin (trade name), fullerene compound, or inorganic materials like silicon oxide, fluosilicate glass, HSQ (Hydrogen Silsesquioxane), MSQ (Methyl Lisesquioxane), porous silica, silicon nitride, aluminum oxide, titanium oxide, calcium fluoride, diamond thin film, etc. These examples may used in any kinds of combination with any percentage of each.

It is also preferred that an insulating and low-permittivity layer (low-permittivity layer) is formed between the interaction-sensing gate and the channel. Further, the portion between the interaction-sensing gate and the channel has preferably low-permittivity characteristic all over (that is, over all of the layers between the interaction-sensing gate and the channel). Here, the phrase "low-permittivity" means that the relative dielectric constant thereof is smaller than 4.5.

Any insulating and low-permittivity materials can be used to construct the low-permittivity layer, as mentioned above, without any other restrictions. Examples thereof are inorganic materials like silicon dioxide, fluosilicate glass, HSQ (Hydrogen Silsesquioxane), MSQ (Methyl Lisesquioxane), porous silica, diamond thin film, and organic materials like polyimide, Parylene-N, Palylene-F, polyimide fluoride, etc. These examples may used in any kinds of combination with any percentage of each.

In fact, because the portion between the channel and the interaction-sensing gate is insulating and low in permittivity, the change of the surface charge on the interaction-sensing gate can be transmitted more efficiently in the form of the density change of the surface change in the channel. Thereby, the above-mentioned interaction can be detected as a wide range of change in the output characteristic of the transistor and thus the sensitivity of the sensor can be further improved when the above-mentioned transistor is used as the sensor.

It is also preferred that an insulating and high-permittivity layer (high-permittivity layer) is formed between the gate for applying a voltage to the transistor and the channel. Further, the portion between the gate and the channel has preferably high-permittivity characteristic all over (that is, over all of the layers between the gate and the channel). Here, the phrase "high-permittivity" means that the relative dielectric constant thereof is bigger than 4.5.

Any insulating and high-permittivity materials can be used to construct the high-permittivity layer, as mentioned above, without any other restrictions. Examples thereof are inorganic materials like silicon nitride, aluminum oxide, tantalum oxide, and polymer materials with high-permittivity characteristic. These examples may used in any kinds of combination with any percentage of each.

In fact, because the portion between the channel and the gate is insulating and high in permittivity, the transfer characteristic of the transistor can be modulated more efficiently with application of gate voltage. Thereby, the sensitivity of the sensor can be further improved when the above-mentioned transistor is used as the sensor.

Next, the channel of the field-effect transistor (hereinafter, called "FET channel", when necessary) and the channel of the single-electron transistor (hereinafter, called "SET channel", when necessary) are explained respectively. The field-effect transistor and the single-electron transistor can be distinguished by the channel of each, as mentioned earlier. In the above embodiments, a transistor should be recognized as a field-effect transistor when it has a FET channel, and as a single-electron transistor when it has a SET channel.

The FET channel may form a current path and any known channels can be used, if necessary. But the size of it is preferred to be minute.

An example of the minute channel is a nano tube structure. The nano tube structure is a structure shaped like a tube, whose size is 0.4 to 50 nm in diameter of the cross section orthogonal to the longitudinal direction. Here, a shape like a tube means a shape with the ratio between the longitudinal length and the longest orthogonal length among all directions is in the range of 10 to 10000. It also includes shapes such as a rod (almost circular in its cross section) or a ribbon (flat and almost square in its cross section).

A nano tube structure can be used as an electric charge transporter. Because it has a structure of one-dimensional quantum wire with several nano meters in diameter, the gate capacitance gets remarkably lowered compared to the field-effect transistors used in conventional sensors. Consequently, the change in the electric potential of the gate, caused by the interaction between the specific substance and the detection targets, gets extremely large. The change in the density of the charged particles existing in the channel gets extremely large, too. Thereby, the sensitivity of the detection for detecting targets is dramatically improved.

Examples of the nano tube structure are a carbon nano tube (CNT), a boron nitride nano tube and a titania nano tube. With the conventional fine processing technology of semiconductors, the detection sensitivity of the sensor has been restricted because of the difficulty in forming 10-nanometer class channel. However, the use of these nano tube structures makes it possible to form channels that are more minute than was previously possible.

A nano tube structure shows an electrical property like either a semiconductor or a metal, depending on its chirality. When it is used as an FET channel like a semiconductor, it is preferred that it has an electrical property like a semiconductor.

The SET channel may also form a current path similarly to the FET channel and any known channels can be used, if necessary. The size of it is also preferred to be minute. Further similarly to the FET channel, a nano tube structure may be used as an SET channel and examples of the nano tube structure are a carbon nano tube (CNT), a boron nitride nano tube and a titania nano tube or the like.

However, the SET channel is different from the FET channel in the point that it has a quantum dot structure. Though any known materials with quantum dot structures can be used as SET channels, usually carbon nano tubes introduced with defects therein are used. More specifically, usually a carbon nano tube with 0.1 to 4 nanometer quantum dot structures between the defects is used. It can be produced by a chemical process such as heating a carbon nano tube without any defects in gas atmosphere like hydrogen, oxygen or argon, or boiling it in acid solution Thus, with these defects introduced in the nano tube structure, the quantum dot structures with regions sized several nanometers are formed between the defects. Thereby, the gate capacitance gets further lowered. A nano tube structure with quantum dot structures shows Coulomb Blockade phenomenon, which blocks the intrusion of electrons into the quantum dot structure, and thus a single-electron transistor can be realized by using that type of nano tube structure.

For example the gate capacitance of conventional silicon base MOSFET (metal-oxide semiconductor field-effect transistor) is about 10-15 F (farad), while the gate capacitance of the above-mentioned single-electron transistor with a nano tube structure introduced with the defects is about 10-19 to 10-20 F. That is, the gate capacitance of a single-electron transistor decreases by a factor of about ten thousand to one hundred thousand, compared to the conventional silicon base MOSFET.

As a result, the change in the gate capacitance, as well as the change in the density of the charged particles in the channel, can be extremely enlarged through the use of a single-electron transistor having a channel formed with the above-mentioned nano tube structure, compared to the conventional field-effect transistor without a nano tube structure. In addition, the detection sensitivity with which the detection targets are detected can be highly improved.

The another point in which the SET channel is different from the FET channel is that the nano tube structure used as the SET channel is preferred to have the electric property like metals. Examples of methods to check if the nano tube structure is like a metal or a semiconductor are the one with which the chirality of the carbon nano tube is determined by Raman spectroscopy or the other with which the electronic state density of the carbon nano tube is measured using scanning tunneling microscope (STM) spectroscopy.

Detection Target and Specific Substance

The detection target is not restricted particularly but any materials can be used. For specific substances (indicated by the numeral reference 10 in the above embodiments), any types of materials may be used as far as they are capable of selectively interacting with the detection targets, without any other restriction. They may be, for example, enzyme, antibody, protein like lectin, peptide, hormone, nucleic acid, sugar, oligosaccharide, sugar chain like polysaccharide, lipid, low molecular compound, organic materials, inorganic materials, or fusion of these materials, and virus, cell, body tissue, or materials composing them, etc.

The protein may be of its full length or may be a partial peptide including a binding activity portion. In addition, the protein with its amino-acid sequence and function known, as well as unknown, may be used. Even synthesized peptide chain, proteins refined from an organism or proteins translated and refined from cDNA library or the like using appropriate translation system can be used as the target molecules. The synthesized peptide chain may be bound with sugar chain to be a glycoprotein. In these examples, the synthesized protein with its amino-acid sequence known or the protein translated and refined from cDNA library or the like using appropriate process are preferably used.

The nucleic acid is not limited particularly, and DNA as well as RNA can be used. The nucleic acid with its base sequence or function known, as well as unknown, may be used. The nucleic acid with its function that it has binding capacity in its protein and its base sequence known or the nucleic acid cut and isolated from genome library or the like using restricted enzyme and the like are preferably used.

The sugar chain with its sugar sequence or function known, as well as unknown, may be used. The sugar chain that is already isolated and analyzed thus with its sugar sequence or function known is preferably used.

The low-molecular compound is not limited particularly, as far as it is capable of interaction. The low molecular with its function unknown, as well as with its capability of bonding or reacting with proteins already known, can be used.

As mentioned above, lots of kinds of specific substances can be immobilized on the interaction-sensing gate. The interaction-sensing gate immobilized specific materials thereon is suitably used for a biosensor used for detection of materials interacting with the functional material. The material, which interacts with the material already interacted with the specific substance, can be marked by enzyme, by materials showing electrochemical reaction or luminous reaction, or by polymer and particles with electric charge. These are well-known method as labeling measurement in the field of DNA analysis using immunoassay or intercalator (cited references: Kazuhiro Imai, "bioluminescence and chemiluminescence," 1989, Hirokawa Shoten or P. TIJSSEN "enzyme immunoassay biochemical experimental technique 11," Tokyo Kagaku Dojin or Takenaka, Anal. Biochem., 218,436 (1994) and the like of many).

The "interaction" between the specific substance and the detection target is not limited particularly, but usually means the action caused by the force acting between the molecules that are combined with at least one type of combinations including covalent bond, hydrophobic bond, hydrogen bond, van der Waals binding or the combination made by electrostatic force. However, the word "interaction" in the present specification should be interpreted most widely and in any meanings it should not be interpreted as limiting. The covalent bond may include coordinate bond and dipolar coupling. The combination made by electrostatic force includes electrostatic repulsion, as well as electrostatic binding. And also the interaction includes reactions occurred by the above-mentioned action, such as binding reaction, synthetic reaction or decomposition reaction.

Examples of the interactions are: binding and dissociation between antigen and antibody, binding and dissociation between protein receptor and ligand, binding and dissociation between adhesion molecule and object molecule, binding and dissociation between enzyme and substrate, binding and dissociation between apoenzyme and coenzyme, binding and dissociation between nucleic acid and protein to be bound thereto, binding and dissociation between nucleic acids, binding and dissociation between proteins in communication system, binding and dissociation between glycoprotein and protein, binding and dissociation between sugar chain and protein, binding and dissociation between cells or body tissues and protein, binding and dissociation between cells or body tissues and low molecule compounds, interaction between ion and ion-sensitive material or the like. However the interaction is not limited to these types of actions, but also includes: immunoglobulin or the derivation F(ab')2, Fab', Fab, receptor or enzyme and the derivation thereof, nucleic acid, native and artificial peptide, artificial polymer, carbohydrate, lipid, inorganic material or organic ligand, virus, cell, drug and the like.

Further, the other examples of the "interaction" between the specific substance immobilized on the interaction-sensing gate and the other material can include the response, related to the functional material immobilized on the gate, not to any substances but to the change in outside environments such as pH, ion, temperature, pressure or the like.

Production Method of Transistor

Next, an example of production method of the transistor, described in the above embodiments, will be explained, using FIG. 7 (*a*) to FIG. 7 (*d*), taking the case that a carbon nano tube is used as the channel for example.

The transistor using a carbon nano tube is produced according to the following procedure.

The carbon nano tube used in the transistor should be manufactured controlling its position and orientation. Thus, it is usually produced using patterned catalyst with a method like photolithography, controlling its position and orientation.

More specifically, a carbon nano tube is produced according to the following steps.

(Step 1) Patterning Photoresist 16 on the Substrate 2, as shown in FIG. 7 (*a*)

The pattern corresponding to the position and the orientation where the carbon nano tube will be formed is determined. Then, the photoresist 16 is patterned according to the determined pattern on the substrate 2.

(Step 2) Evaporation Metal Catalyst 17, as shown in FIG. 7 (*b*)

A metal that will be catalyst 17 is evaporated onto the patterned substrate 2. Examples of the metal to be catalyst 17 are transition metals like iron, nickel or cobalt, the alloys of them, etc.

(Step 3) Liftoff to Pattern with catalyst 17, as shown in FIG. 7 (*c*)

After the evaporation of the catalyst 17, lift-off is performed. The photoresist 16, as well as the catalyst 17 evaporated on the surface of the photoresist 16, are removed from the substrate 2 by the lift-off. Thereby, the pattern of the catalyst 17 is made according to the pattern formed in step 1.

(Step 4) Feed the Gas like Methane Gas or Alcohol Gas in CVD (chemical vapor deposition) furnace 18 at high temperature and forming carbon nano tube 19 between the Catalysts 17, as shown in FIG. 7 (*d*)

At high temperature, metallic catalyst 17 turns to be minute particles of several nanometers in diameter, which is used as the core around which the carbon nano tube grows. Here, the high temperature usually means from 300 to 1200° C.

After forming the carbon nano tube 19 following the steps 1 to 4, the source electrode and the drain electrode are produced at the both edge of the carbon nano tube 19. In this explanation, ohmic electrodes are formed as the source electrode and the drain electrode. At this point, the source electrode and the drain electrode can be installed at the tips of the carbon nano tube 19 or at the lateral side thereof. The heat treatment in the range of 300 to 1000° C. can be made when the source electrode and the drain electrode are formed so as to get the improved condition of the electrical connections.

Then, the gate and the interaction-sensing gate are provided at appropriate positions, to finish the production of the transistor.

Figure 8:
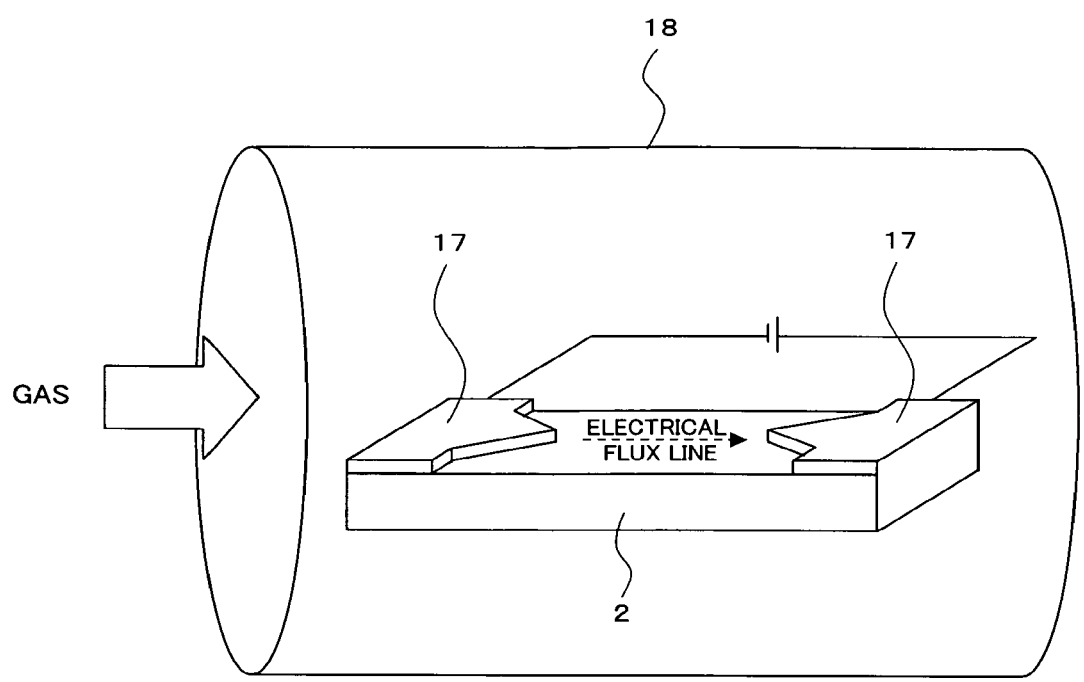
FIG. 8 is a figure illustrating an example of producting method of a transistor according to an embodiment of the present invention.

According to the above-mentioned method of production, the transistor can be produced forming the carbon nano tube 19 under control of the position and the orientation thereof. However, the probability of forming the carbon nano tube 19 between the catalyst metals is small by above-mentioned method of production (about 10% in the test performed by the present inventors). So, as shown in FIG. 8, the shape of the catalysts 17 are made to be pointed sharply and an electric charge is applied between the two catalysts while the carbon nano tube 19 is growing. This raises expectations that the carbon nano tube 19 grows between the sharp catalysts along the electrical flux line.

The reason why the carbon nano tube 19 grows when an electric charge is applied between the catalysts 17 is not yet understood. However, the following two reasons are guessed. One is that the carbon nano tube 19, starting to grow from the electrode (catalyst 17, in this example), has large polarization moment and thus it grows along the direction of the electric field. The other is that the carbon ions decomposited at high temperature form the carbon nano tube 19 along the electrical flux line.

Figure 9:
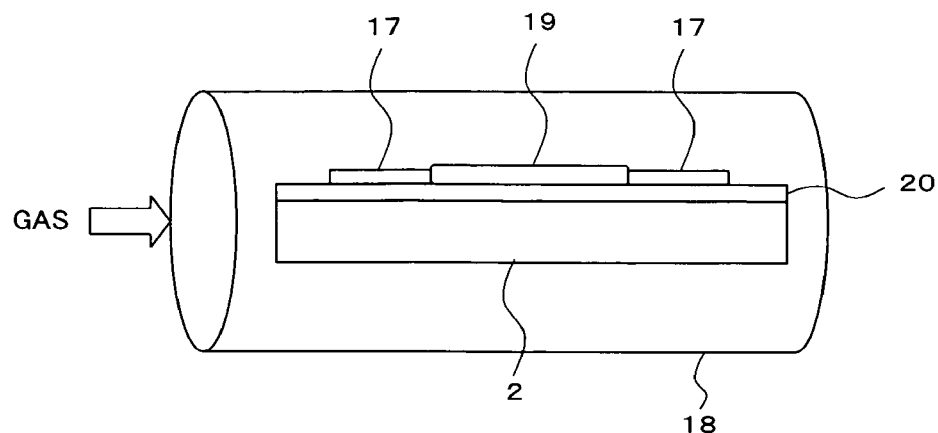
FIG. 9 is a figure illustrating an example of producting method of a transistor according to an embodiment of the present invention.

Also it is probable that large Van der Waals force between the substrate 2 and the carbon nano tube 19 may inhibit the growth of the carbon nano tube 19. The carbon nano tube 19 may be attracted to get close to the substrate 2 by Van der Waals force and the controlling of the direction thereof may be troubled. Thus, it is preferable to form the spacer layer 20 of silicon oxide or the like between the catalyst 17 and the substrate 2, as shown in FIG. 9, which can make the carbon nano tube 19 apart from the substrate 2 during the growth thereof.

According to the above-mentioned process, the field-effect transistor can be produced.

Then, the single-electron transistor can be manufactured from the field-effect transistor by chemical treatings such as heating in atmosphere gas of hydrogen, oxygen or argon, or boiling in the acid solution so as to introduce the defects for forming quantum dot structure therein.

Immobilizing Method of Specific Substance to Interaction-Sensing Gate

The method of immobilizing the specific substance to the interaction-sensing gate is not limited particularly, as far as the immobilization can be done with the method. The substance can be binded directly to the interaction-sensing gate by physical adsorption, or by a flexible spacer, which has an anchor portion to bind the substance, placed at the interaction-sensing gate in advance, for example.

When a metal is used for the interaction-sensing gate, the flexible spacer includes preferably alkylene with structural formula $(CH2)n$ (n shows a natural number 1 to 30, preferably 2 to 30, more preferably 2 to 15). The thiol group or the disulfide group, which forms an anchor portion suitable for adsorption of metals like gold, is preferably used for one end of the spacer molecule. One or more connecting portions that can bind the specific substance to be immobilized are preferably included in the other end of the spacer molecule, which points to the other directions than to the interaction-sensing gate. The connecting portion may be various reactive functional group such as amino group, carboxyl group, hydroxyl group, suximide group, and hapten or chelate such as biotin, biotin derivative, digoxin, digoxigenin, fluorescein, fluorescein derivative, theophylline, for example.

In order for the specific substance to be immobilized to the interaction-sensing gate, we can first bind conductive polymer, hydrophilic polymer, LB membrane or matrix to the interaction-sensing gate, directly or with a spacer therebetween, and then can connect, include or support one or more kinds of the specific substance on the conductive polymer, hydrophilic polymer, LB membrane or matrix. And also, we can first connect, include or support one or more kinds of the specific substance on them and then can bind it to the interaction-sensing gate.

The conductive polymer may be, for example, polypyrrole, polythiophene, polyaniline or the like. The hydrophilic polymer may be polymer without any electric charge such as dextran or polyethylene oxide, and may be polymer with electric charge such as polyacrylic acid or carboxyl methyl dextran. In the case of polymer with electric charge, with the use of the polymer with opposite electric charge to the specific substance to be immobilized, the specific substance can be connected or supported utilizing electric charge enrichment effect (cited document: farumashia patent, Japanese Patent No. 2814639).

For detecting a specific ion, an ion-sensitive membrane corresponding to the specific ion can be formed on the interaction-sensing gate. In addition, the enzyme immobilization membrane can be formed instead of or together with the ion-sensitive membrane. This results in that the detection target can be detected by means of measuring the product of enzyme, acted as a catalyst toward the detection target.

After immobilization of the specific substance to be immobilized, surface processing using inert molecules such as bovine serum albumin, polyethylene oxide or the like, covering with UF membrane in order to inhibit nonspecific reaction, or selecting permeable materials can be done.

An insulating membrane can be selected as the interaction-sensing gate, other than metals. Examples of the materials used for the insulating membrane are inorganic materials such as silicon oxide, silicon nitride, aluminum oxide, titanium oxide, calcium fluoride, and polymer such as acrylic resin, epoxy resin, polyimide resin, Teflon (registered trademark), etc.

In order to measure ions like H+ or Na+, an ion-sensitive membrane can be formed on the insulating membrane, if necessary, corresponding to the respective ions to be detected. In addition, the enzyme immobilization membrane can be formed instead of or together with the ion-sensitive membrane. This results in that the detection target can be detected by means of measuring the product of enzyme, acted as a catalyst toward the detection target (cited documents: Syuichi Suzuki "Biosensor" 1984 Kodansha and Karube et al. "Development and practical application of Sensor," vol. 30 No. 1 Bessatsu Kagaku Kogyo 1986).

Application Areas

The sensor of the present invention can be used in any appropriate area. Specific examples are in the following.

When it is used as a biosensor utilizing interactions, for example a sensor for clinical examination on blood, urine or the like, pH, electrolyte, dissolved gas, organic materials, hormone, allergen, medication, antibiotic, activity of the enzymes, protein, peptide, mutagenic materials, cell of microorganism, blood cell, blood type, hemostasis, DNA analysis can be measured. In the point of the principle of measuring, examples of sensors to be considered are ion sensor, enzyme sensor, microorganism sensor, immune sensor, enzyme immune sensor, luminescent immune sensor, fungi count sensor, blood clotting electrochemical sensing and electrochemical sensor using various electrochemical reactions. However it can contain all the principles with which an electric signal can be available as the final output (cited documents: Syuichi Suzuki "Biosensor" Kodansha (1984) and Karube et al. "Development and practical application of Sensor," vol. 30 No. 1 Bessatsu Kagaku Kogyo (1986)).

Furthermore, the sensor of the present invention can be used in the measurement in vivo and in situ, for example an insertion-type microsensor mounted on a catheter, implantable microsensor or capsule-mounted type microsensor using medical capsule (cited document: Karube et al. "Development and practical application of Sensor," vol. 30 No. 1 Bessatsu Kagaku Kogyo 1986).

Examples

In the following, examples of the present invention will be described referring to the Figs. An field-effect transistor with a carbon nano tube as the channel was produced like the following.

1. Production of the Sensor

Preparation of the Substrate

After oxidating the surface of an n-type Si(100) substrate 2 by dipping it into an acid with the volume ratio between sulfuric acid and hydrogen peroxide is 4:1 for five minutes, it was rinsed out with water for five minutes. Then the oxicide layer was removed with acid with the volume ratio between hydrogen fluoride and pure water is 1:4, and finally it was rinsed out to wash the surface of the Si substrate. Then the surface of the Si substrate 2 washed was thermally-oxidized with an oxidization furnace under the condition of 1100° C. temperature for 30 minutes with enzyme flow rate 3 L per minute. Consequently the insulating membrane 20 was formed with about 100 nanometers-thickness of SiO2.

Formation of the Channel

Figure 10A:
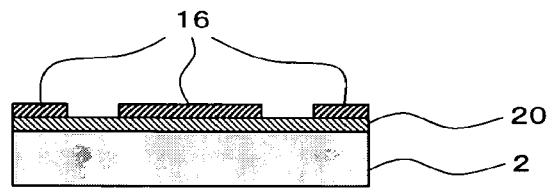
FIG. 10 (*a*) to FIG. 10 (*c*) are figures illustrating examples of the present invention.
Figure 10B:
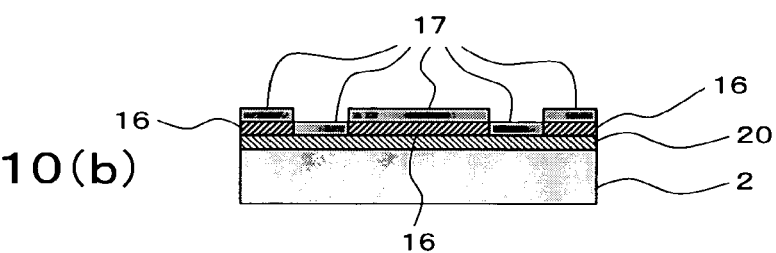
Figure 10C:
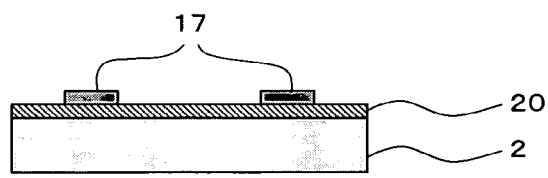

Next, the photoresist 16 was patterned by a photolithography method so as to form a carbon nano tube growth catalyst on the surface of the insulating layer 20 {FIG. 10(*a*)}. First, the hexamethyldisilazane (HMDS) was spin coated on the insulating layer 20 under the condition of 500 rpm for ten seconds, then 4000 rpm for 30 seconds. Then the photoresist (microposit "S1818" manufactured by Shipley Far East Ltd.) was spin coated under the same condition.

After the spin coat, the Si substrate 2 is baked on a hot plate under at the temperature of 90° C. for one minute. Then, the Si substrate 2 coated with photoresist 16 was dipped into monochlorobenzene and after that it was dried by nitrogen brow. Then it was baked in an oven at the temperature of 85° C. for five minutes. After the baking, it was exposed with a patternend enzyme using an aligner and then was developed for four minutes in developing agent ("AZ300MIF developer (2.38%)" manufactured by Clariant Co.). Then it was rinsed out with flowing water for three minutes and was dried by nitrogen brow.

The Si, Mo and Fe catalyst 17 is deposited on the Si substrate 2 patterned with the photoresist 16 using an EB vacuum evaporation system in order for the thicknesses of Si, Mo and Fe to be 100 Å, 100 Å and 30 Å respectively, with deposition rate of 1 Å per second {FIG. 10(*b*)}. After the deposition, the lift-off was done in acetone which is being boiled. Then it was washed by acetone, then by ethanol, and finally by flowing water, each for three minutes, and was dried by nitrogen brow {FIG. 10(*c*)}.

The Si substrate 2 patterned with the catalyst 17 was set in a CVD furnace and blowed with ethanol, bubbled with Ar, with the rate of 750 cc per minute and hydrogen with the rate of 500 cc per minute, at the temperature of 900° C. for 20 minutes so as to make the carbon nano tube 19 grow, which will be the channel (FIG. 11). In this process, heating up and cooling down are done with Ar being blown at the rate of 1000 cc per minute.

Production of the Source, Drain and Side Electrodes

After the growth of the carbon nano tube, the photoresist 16 was patterned on the Si substrate 2 by a photolithography method, mentioned above, so as to product the source electrode, drain electrode and side gate {FIG. 12(*a*)}.

After the patterning, Ti and then Au are deposited on the Si substrate 2, so as to form the source electrode 4, drain electrode 5 and side gate electrode 7, using an EB vacuum evaporation system with the thicknesses of Ti and Au to be 300 Å and 3000 Å respectively and with the deposition rates of 0.5 Å and 5 Å per second respectively {FIG. 12(*b*)}. After the deposition, the same as in the above-mentioned method, the lift-off was done in acetone that is being boiled. Then it was washed by acetone, then by ethanol, and finally by flowing water, each for three minutes, and was dried by nitrogen brow {FIG. 12(*c*)}.

After the patterning of the source electrode 4, drain electrode 5 and side gate electrode 7, HMDS is spin coated on the right side of the Si substrate 2, so as to protect the elements, under the condition of 500 rpm for ten seconds, then 4000 rpm for 30 seconds. Then the above-mentioned photoresist was spin coated under the same condition. Then the photoresist was hardened in an oven at the temperature 110° C. for 30 minutes so as to form a layer protecting the elements.

Production of the Back Gate

Figure 13:
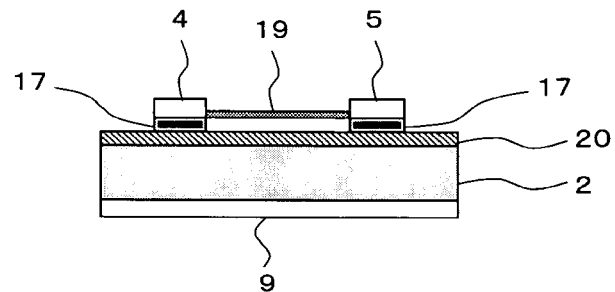
FIG. 13 is a figure illustrating examples of the present invention.

The SiO2 layer 20 on the back side of the Si substrate 2 was removed by dry etching using RIE (reactive ion etching) device. Here, SF6 was used for etchant and etching was done for six minutes in plasma with the RF power of 100 W. After removing the SiO2 layer 20 on the back side, Pt and then Au are deposited on the Si substrate 2, so as to form the back gate electrode (interaction-sensing gate) 9, using an EB vacuum evaporation system with the thicknesses of Pt and Au to be 300 Å and 2000 Å respectively and with the deposition rates of 0.5 Å and 5 Å per second respectively (FIG. 13).

Formation of the Channel Layer

Figure 14:
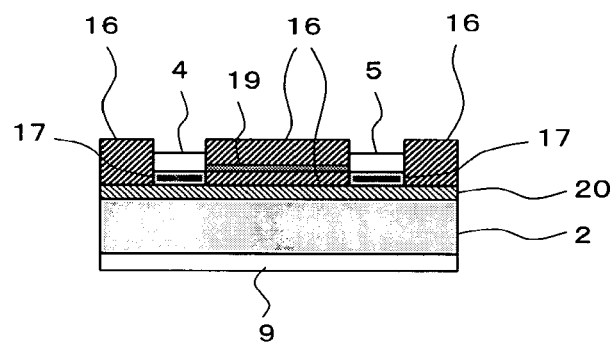
FIG. 14 is a figure illustrating examples of the present invention.
Figure 15:
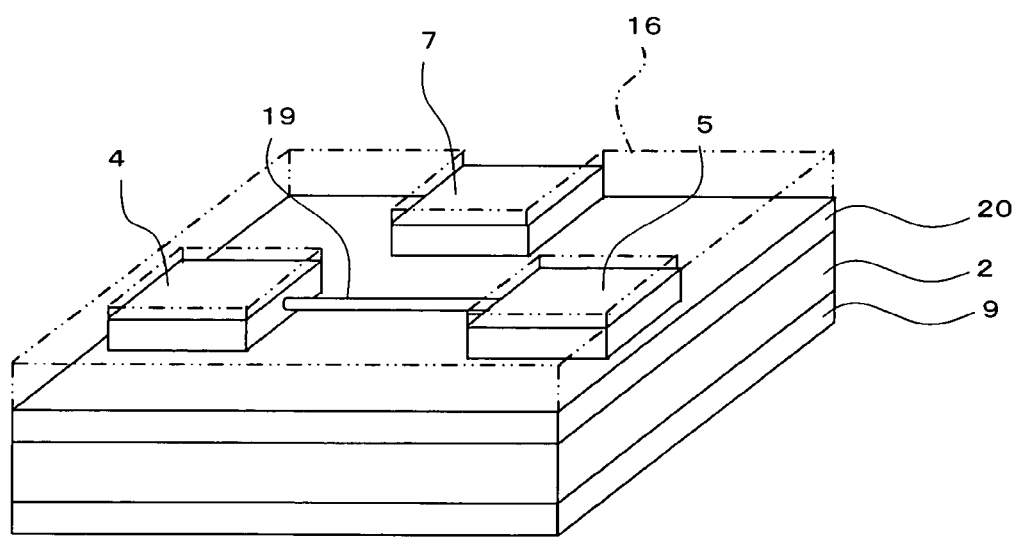
FIG. 15 is a figure illustrating examples of the present invention.

Then the layer protecting the elements formed on the Si substrate 2 was removed by being washed in acetone being boiled, then by acetone, ethanol, and finally by flowing water each for three minutes. Next, the photoresist was patterned, similarly to the photolithography method used for patterning the source electrode 4, drain electrode 5 and side gate electrode 7, onto the right side of the elements in the area without the source electrode 4, drain electrode 5 and side gate electrode 7, so as to form the channel protecting layer 16 (FIG. 14). The schematic diagram of the carbon nano tube-field effect transistor (hereinafter, called "CNT-FET" when necessary) produced by above-mentioned method is shown in FIG. 15.

2. Characteristic Measurement Using the Sensor

Using the CNT-FET produced, the characteristic before and after immobilization of the antibody was measured according to the following process.

Figure 16:
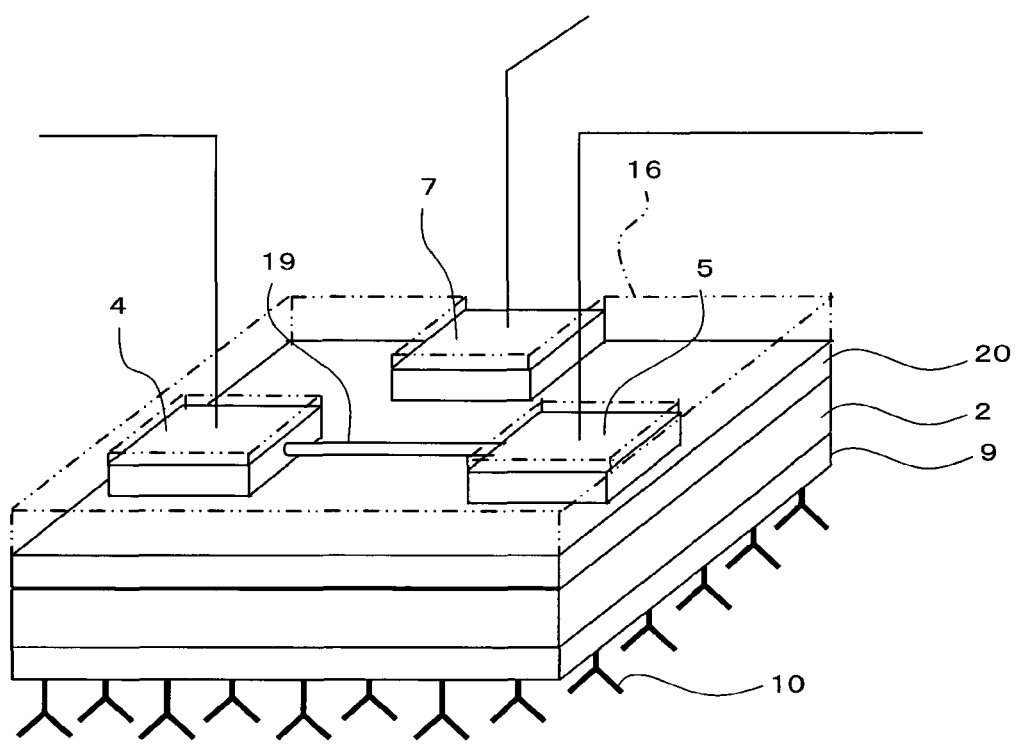
FIG. 16 is a figure illustrating examples of the present invention.

Fifty microliters of the mouse IgG antibody solution, which is diluted by acetic acid buffer solution to have concentration of 100 [microgram/milliliter], was dropped on the back gate 9, in order for the antibody to be immobilized, through the reaction in a wetting box at the humidity of 90% for 15 minutes and the washing with pure water the surface thereof. As the result of the immobilization, the specific substance, IgG antibody 10, was immobilized on the back gate electrode 9, as shown in FIG. 16. The channel-protecting layer 16 is shown by chain double-dashed line in FIG. 16.

The measurement of electric characteristic of CNT-FET was conducted using the semiconductor parameter analyzer 4156C manufactured by Agilent Co. The transfer characteristic (VSG-ISD characteristic), which is a kind of electric characteristic, was measured before and after the immobilization of the antibody and then the two measured values were compared. The result of the measurement is shown in FIG. 16. In the measurement, at each stepped point of the side gate voltage VSG, which was sweeped from −40 to 40 V (stepped by 0.8 V), the current that flows between the source electrode and the drain electrode (source drain current) ISD A was measured while the source voltage VS was maintained to 0 V and the drain voltage VD was swept −1 to 1 V (stepped by 0.02 V). In FIG. 17, the graph lines of negative in the value of source drain current indicates the measured value while VSD is −1.0 V and the graph lines of positive in the value of source drain current indicates the measured value while VSD is +1.0 V.

To note the portion around 5 microamperes in the value of source drain current in FIG. 17, the side gate voltage after the immobilization of the antibody increased with +47 V from before the immobilization of the antibody, the change of which was remarkable. The measurement resulted in that the interaction occurred in the vicinity of the back gate can be directly measured because the transfer characteristic of CNT-FET is dramatically changed between before and after the immobilization of the antibody. This result indicates that the sensor of the present invention has extremely high sensitivity with which it detects chemicals and thus it is easily expected that the sensor is capable of detecting the interaction between the detection target and the specific substance.

INDUSTRIAL APPLICABILITY

The present invention can be applied to wide range of analysis such as chemical analysis, physical analysis or biological analysis, and is suitably used for a medical sensor or a biosensor for example.

What is claimed is:

1. A method of detecting a detection target using a sensor, the sensor comprising a transistor selected from the group of field-effect transistors or single electron transistors, the transistor comprising
    a substrate having a first side and a second side, the second side being opposed to the first side, the substrate being formed of an insulating material,
    a source electrode disposed on the first side of the substrate and a drain electrode disposed on the first side of the substrate, and
    a channel forming a current path between the source electrode and the drain electrode;
    an interaction-sensing gate disposed on the second side of the entire substrate, the interaction-sensing gate immobilizing a specific substance that is capable of selectively interacting with the detection target, the interaction-sensing gate being formed of a conductor; and
    a gate disposed on the side of the channel on the first side of the substrate;
the method comprising the steps of:
    (a) providing the detection target on the interaction-sensing gate;
    (b) setting a gate voltage in the gate in such a state that a transconductance of the transistor reaches a highest level;
    (c) selectively interacting the specific substance with the detection target;
    (d) when the detection target interacts with the specific substance, changing an electric potential of the interaction-sensing gate which leads to a change in a characteristic value of the transistor; and
    (e) measuring the change in the characteristic value of the transistor to determine a presence of the detection target.

2. The method of claim 1, wherein step (b) comprises setting the gate voltage such that the change of the characteristic value of the transistor is expected to reach the sufficient level on the detection of the detection target.

3. The method of claim 2, wherein the sensor comprises the field-effect transistor, and the change in the characteristic value of the transistor is a current that flows between the source electrode and the drain electrode.

4. The method of claim 2, wherein the change in the characteristic value of the transistor is a side gate voltage.

* * * * *